US009867923B2

(12) United States Patent
Reiser

(10) Patent No.: US 9,867,923 B2
(45) Date of Patent: Jan. 16, 2018

(54) REDUCING SOLUBLE UROKINASE RECEPTOR IN THE CIRCULATION

(75) Inventor: Jochen Reiser, Hinsdale, IL (US)

(73) Assignee: University of Miami, Miami, FL (US)

( * ) Notice: Subject to any disclaimer, the term of this patent is extended or adjusted under 35 U.S.C. 154(b) by 554 days.

(21) Appl. No.: 14/116,470

(22) PCT Filed: May 9, 2012

(86) PCT No.: PCT/US2012/000240
§ 371 (c)(1),
(2), (4) Date: Nov. 8, 2013

(87) PCT Pub. No.: WO2012/154218
PCT Pub. Date: Nov. 15, 2012

(65) Prior Publication Data
US 2014/0083945 A1    Mar. 27, 2014

Related U.S. Application Data

(60) Provisional application No. 61/457,665, filed on May 9, 2011.

(51) Int. Cl.
*A61M 1/34* (2006.01)
*A61M 1/36* (2006.01)
(Continued)

(52) U.S. Cl.
CPC .......... *A61M 1/3486* (2014.02); *A61K 35/16* (2013.01); *A61K 38/177* (2013.01);
(Continued)

(58) Field of Classification Search
CPC ... A61K 35/16; A61K 38/177; A61M 1/3486; A61M 1/3496; A61M 1/362;
(Continued)

(56) References Cited

U.S. PATENT DOCUMENTS

2004/0265797 A1   12/2004   Rosenberg et al.
2005/0265996 A1*  12/2005   Lentz .................. A61M 1/3472
                                                 424/141.1
(Continued)

FOREIGN PATENT DOCUMENTS

RU    2311183    11/2007
RU    2378016     1/2010
(Continued)

OTHER PUBLICATIONS

Dantal J. et al, New England Journal of Medicine 1994; 330:7-14 (Jan. 6, 1994).*
(Continued)

*Primary Examiner* — John Kim
(74) *Attorney, Agent, or Firm* — Fish & Richardson P.C.

(57) ABSTRACT

Focal segmental glomerulosclerosis (FSGS) is a common cause of proteinuric kidney disease, which comprises both native and transplanted kidneys. Treatment was limited in the past due to the complicated pathogenesis of FSGS, including previously unidentified serum factors. Here, serum soluble urokinase receptor (suPAR) is reported to be elevated in FSGS patients but not in patients with other primary glomerular diseases. Higher pre-transplantation suPAR levels are associated with risk for FSGS recurrence in kidney grafts. Renal disease only develops when suPAR sufficiently activates podocyte β3 integrin. Thus, disease pathogenesis can be stopped or slowed by ex vivo removal of suPAR from a subject's circulation. Removal may be measured by comparing the level (e.g., amount or concentration) of suPAR before and after such treatment.

18 Claims, 6 Drawing Sheets

(51) Int. Cl.
G01N 33/68 (2006.01)
A61K 35/16 (2015.01)
C07K 14/705 (2006.01)
A61K 38/17 (2006.01)

(52) U.S. Cl.
CPC .......... A61M 1/3496 (2013.01); A61M 1/362 (2014.02); A61M 1/3672 (2013.01); A61M 1/3687 (2013.01); C07K 14/70596 (2013.01); G01N 33/6872 (2013.01); A61M 1/3679 (2013.01)

(58) Field of Classification Search
CPC .............. A61M 1/3672; A61M 1/3679; A61M 1/3687; C07K 14/70596; G01N 33/6872
See application file for complete search history.

(56) References Cited

U.S. PATENT DOCUMENTS

| | | | |
|---|---|---|---|
| 2006/0240437 | A1 | 10/2006 | Krolewski et al. |
| 2007/0068870 | A1* | 3/2007 | Johnson .............. A61M 1/3679 210/645 |
| 2007/0244046 | A1 | 10/2007 | Gutova et al. |
| 2007/0249002 | A1 | 10/2007 | Hu et al. |
| 2008/0152587 | A1 | 6/2008 | Zhou et al. |
| 2010/0098705 | A1 | 4/2010 | Eugen-Olsen et al. |
| 2010/0297139 | A1 | 11/2010 | Reiser |
| 2011/0212083 | A1 | 9/2011 | Reiser |

FOREIGN PATENT DOCUMENTS

| | | |
|---|---|---|
| WO | 1998/21230 | 5/1998 |
| WO | WO200123413 | 4/2001 |
| WO | 2005/107802 A2 | 11/2005 |
| WO | 2005/116077 | 12/2005 |
| WO | 2007/056435 | 5/2007 |
| WO | 2008/077958 | 7/2008 |
| WO | 2009/055613 | 4/2009 |
| WO | 2010/054189 | 5/2010 |
| WO | WO2012154218 | 11/2012 |

OTHER PUBLICATIONS

Coffman et al., "Improved renal function in mouse kidney allografts lacking MHC class I antigens" J. Immunol. 151:425-435, 1993 (Abstract Only).
Crowley et al., "Glomerular type 1 angiotensin receptors augment kidney injury and inflammation in murine autoimmune nephritis" J. Clin. Invest. 119:943-953, 2009.
Dantal et al., "Antihuman immunoglobulin affinity immunoadsorption strongly decreases proteinuria in patients with relapsing nephrotic syndrome" J. Am. Soc. Nephrol. 9:1709-1715, 1998.
De Smet et al., "FSGS permeability factor-associated nephrotic syndrome: remission after oral galactose therapy" Nephrol Dial. Transplant. 24:2938-2940, 2009.
Genbank Accession No. BC010309, "Mus musculus, urokinase plasminogen activator receptor, clone MGC:11631 IMAGE:3158012, mRNA, complete cds," dated Oct. 29, 2011, 2 pages.
Genbank Accession No. NM_011113, "Mus musculus urokinase plasminogen activator receptor (Plaur), mRNA," dated Mar. 8, 2000, 2 pages.
Genbank Accession No. NM_016780, "Mus musculus integrin beta 3 (Cd61) (Itgb3), mRNA," dated May 12, 2000, 3 pages.
International Preliminary Report on Patentability in International Application No. PCT/US2012/000240, dated Nov. 12, 2013, 6 pages.
International Search Report and Written Opinion in International Application No. PCT/US2012/000240, dated Oct. 18, 2012, 8 pages.
Levey et al., "A new equation to estimate glomerular filtration rate" Ann. Intern. Med. 150:604-612, 2009.
Saleem et al., "A conditionally immortalized human podocyte cell line demonstrating nephrin and podocin expression" J. Am. Soc. Nephrol. 13:630-638, 2002.
Salido et al., "The P1A2 polymorphism of the platelet glycoprotein IIIA gene as a risk factor for acute renal allograft rejection" J. Am. Soc. Nephrol. 10:2599-2605, 1999.
Savin et al., "Galactose binds to focal segmental glomerulosclerosis permeability factor and inhibits its activity" Translational Res. 151:288-292, 2008 (Abstract Only).
Tjwa et al., "Membrane-anchored uPAR regulates the proliferation, marrow pool size, engraftment, and mobilization of mouse hematopoietic stem/progenitor cells" J. Clin. Invest. 119:1008-1018, 2009.
European Patent Office, "Extended Search Report", Feb. 9, 2012, pp. 1-8.
Piccolella et al., "suPAR, a soluble form of urokinase plasminogen activator receptor, inhibits human prostate cancer cell growth and invasion" International Journal of Oncology (Jan. 2008) 32(1):185-191.
Wittenhagen, P., et al. "The plasma level of soluble urokinase receptor is elevated in patients with *Streptococcus pneumoniae* bacteraemia and predicts mortality," Clin. Microbiol. Infect. (May 2004) 10(5):409-415.
Written Opinion of the International Searching Authority (US) for International Application No. PCT/US09/63542, opinion completed Feb. 8, 2010.
Piironen Timo et al: "Enhanced discrimination of benign from malignant prostatic disease by selective measurements of cleaved forms of urokinase receptor in serum". Clinical Chemistry, American Association for Clinical Chemistry, Washington, DC, vol. 52, No. 5, May 1, 2006 (May 1, 2006), pp. 838-844, for XP002614528.
Piironen Timo et al: "Specific immunoassays for detection of intact and cleaved forms of the urokinase receptor", Clincal Chemistry, Washington, DC, vol. 40, No. 11, Nov. 1, 2004 (Nov. 1, 2004), pp. 2059-2068. XP002614529.
McCarthy et al., "Circulating Permeability Factors in Idiopathic Nephrotic Syndrome and Focal Segmental Glomerulosclerosis" Clin J. Am Soc Nephrol (2010) 5:2115-2121.
Wei et al., "Modification of kidney barrier function by the urokinase receptor" Nature Medicine (2007) 14(1):55-63.
Dantal et al., "Effect of Plasma Protein Adsorption on Protein Excretion in Kidney-Transplant Recipients With Recurrent Nephrotic Syndrome," New England Journal of Medicine, Jan. 1994, 330: 7-14.
Davenport, "Apheresis treatment of recurrent focal segmental glomerulosclerosis after kidney transplantation: Re-analysis of published case-reports and case-series," Journal of Clinical Apheresis, Jan. 2001, 16: 175-178.
European Office Action in European Application No. 12782210, dated Oct. 21, 2016, 6 pages.
European Office Action in Application No. 12782210.4, dated Jun. 23, 2017, 6 pages.

* cited by examiner

Active β3 integrin (AP5 staining) in renal biopsies

| Disease | Glomerulus number | % Focal Sclerosis | % AP5 Positive Glomeruli |
|---|---|---|---|
| Control (n=3) | 32.7 ± 4.2 | 0.0 ± 0.0 | 0.0 ± 0.0 |
| FSGS Primary (n=9) | 10.1 ± 2.3 | 31 ± 7.3 | 60.2 ± 39.3 * |
| FSGS recurrent (n=6) | 9.3 ± 1.0 | 31.8 ± 5.4 | 77.8 ± 18.5 ** |
| MCD (n=5) | 10 ± 1.4 | 0.0 ± 0.0 | 17 ± 21.1 |
| MN (n=5) | 10 ± 1.6 | 0.0 ± 0.0 | 10.8 ± 19.1 |

Figure 3

Pathology Score

| | Glomerulus (Intensity 0-4; Focal 0-4) | | | | | Tubule (Intensity 0-4; Focal 0-4) | Interstitium (Intensity 0-4; Focal 0-4) |
|---|---|---|---|---|---|---|---|
| | Focal Hypercellularity | Podocyte Reactivity | Adhesion | Hyperlobulation | Subtotal | Protein Deposition | Chronic Inflammation |
| suPAR | 4.3 ± 0.6 | 3.0 ± 1.0 | 1.3 ± 0.6 | 2.0 ± 0.0 | 10.7 ± 1.5 | 1.7 ± 0.6 | 0.7 ± 0.6 |
| E134A | 1.3 ± 0.6 | 0.0 ± 0.0 | 0.0 ± 0.0 | 0.0 ± 0.0 | 1.3 ± 0.6 | 1.3 ± 0.6 | 0.0 ± 0.0 |

Figure 4

Kidney pathological score

| | Glomerulus (Intensity 0-4; Focal 0-4) | | | | | Tubule (Intensity 0-4; Focal 0-4) | Interstitium (Intensity 0-4; Focal 0-4) |
|---|---|---|---|---|---|---|---|
| | Focal Hypercellularity | Podocyte Reactivity | Adhesion | Hyperlobulation | Subtotal | Protein Deposition | Chronic Inflammation |
| suPAR/ IgG Con | 4.0 ± 0.0 | 2.0 ± 0.0 | 2.7 ± 1.1 | 0.7 ± 0.0 | 9.3 ± 1.5 | 0.0 ± 0.0 | 0.7 ± 0.6 |
| suPAR/ uPAR Mab | 1.7 ± 0.6 | 1.0 ± 0.0 | 0.3 ± 0.6 | 0.0 ± 0.0 | 3.0 ± 1.0 | 0.0 ± 0.6 | 0.0 ± 0.0 |

Figure 5

| Age (years) and sex distribution of the study population | | | |
|---|---|---|---|
| | Control | FSGS-CT | PodoNet |
| Age at sampling | | | |
| 0-2 | 12 | | 8 |
| 3-12 | 62 | 17 | 55 |
| 13-18 | 36 | 27 | 31 |
| >18 | | 26 | |
| Age at disease onset | | | |
| 0-2 | | 1 | 29 |
| 3-12 | | 20 | 53 |
| 13-18 | | 24 | 12 |
| >18 | | 25 | |
| Sex | | | |
| Female | 50 | 31 | 56 |
| Male | 50 | 39 | 38 |

Figure 6

Multiple regression analysis of suPAR in FSGS-CT

|  | P value | |
| --- | --- | --- |
|  | suPAR W01 | suPAR W26 |
| Age Onset | 0.06 | 0.98 |
| Age Sampling | 0.15 | 0.58 |
| Sex | 0.06 | 0.33 |
| Race | 0.73 | 0.07 |
| Up/c W01 | 0.52 | 0.05 |
| Serum Albumin W01 | 0.81 | 0.02 |
| Serum creatinine W01 | 0.12 | 0.86 |
| eGFR W01 | 0.24 | 0.83 |
| Up/c W26 |  | 0.02 |
| Serum Albumin W26 |  | 0.02 |
| Serum creatinine W26 |  | 0.95 |
| eGFR W26 |  | 0.06 |

Figure 7

FSGS CT baseline characteristics by treatment, univariate analysis

|  | CSA (N=35) | MMF (N=35) | p Value |
|---|---|---|---|
| Age onset | 18.43 ± 1.76 | 17.29 ± 1.65 | 0.60 |
| Age sampling | 19.89 ± 1.79 | 18.26 ± 1.64 | 0.47 |
| Female (%) | 13 (37.14%) | 18 (51.42%) | 0.28 |
| Black race | 11 (31%) | 12 (34%) | 0.50 |
| Up/c (g/g) | 5.41 ± 0.77 | 4.59 ± 0.53 | 0.40 |
| Serum albumin (mg/dl) | 3.07 ± 0.15 | 3.13 ± 0.13 | 0.90 |
| Serum creatinine (mg/dl) | 1.18 ± 0.12 | 1.00 ± 0.09 | 0.25 |
| eGFR | 118.20 ± 10.34 | 122.60 ± 9.24 | 0.53 |
| suPAR (pg/ml) | 4721 ± 319.9 | 4311 ± 224.4 | 0.36 |

Figure 8

PodoNet characteristics by etiology

| | Gen/Fam (N=28) | Non-Genetic (N=66) | p Value |
|---|---|---|---|
| Age onset | 5.24 ± 0.78 | 6.41 ± 0.56 | 0.22 |
| Age sampling | 8.36 ± 1.06 | 10.53 ± 0.63 | 0.06 |
| Female (%) | 20 (71.42%) | 36 (54.54%) | 0.13 |
| Proteinuria (g/m$^2$/d) | 3.27 ± 0.76 | 1.68 ± 0.35 | 0.03 |
| Serum albumin (mg/dl) | 2.96 ± 0.21 | 3.43 ± 0.13 | 0.07 |
| Serum creatinine (mg/dl) | 0.91 ± 0.13 | 0.69 ± 0.07 | 0.19 |
| eGFR | 104.9 ± 20.86 | 110.2 ± 9.29 | 0.06 |

Figure 9

PodoNet characteristics by treatment

| | MMF (N=17) | Others (N=77) | p Value |
|---|---|---|---|
| Age onset | 4.83 ± 0.99 | 6.41 ± 0.51 | 0.17 |
| Age sampling | 11.07 ± 1.29 | 9.62 ± 0.60 | 0.22 |
| Female (%) | 8 (47.05%) | 48 (62.33%) | 0.13 |
| Proteinuria (g/m$^2$/d) | 1.59 ± 0.68 | 2.25 ± 0.39 | 0.18 |
| Serum albumin (mg/dl) | 3.21 ± 0.31 | 3.31 ± 0.12 | 0.86 |
| Serum creatinine (mg/dl) | 0.82 ± 0.13 | 0.74 ± 0.07 | 0.66 |
| eGFR | 91.60 ± 10.82 | 112.2 ± 10.90 | 0.89 |

REDUCING SOLUBLE UROKINASE RECEPTOR IN THE CIRCULATION

RELATED APPLICATIONS

This application claims priority benefit of provisional patent application, U.S. Ser. No. 61/457,665, filed 9 May 2011; the contents of which are incorporated by reference herein.

FEDERAL GOVERNMENT SUPPORT

This invention was made with government support under DK073495 and DK089394 awarded by the National Institutes of Health. The government has certain rights in the invention.

BACKGROUND

An objective is reducing the level (e.g., amount or concentration as measured before and after treatment) of circulating soluble urokinase receptor (suPAR) as therapy for kidney disease or its prevention.

Focal segmental glomerulosclerosis (FSGS) is a significant cause of end-stage kidney disease. It affects both native kidneys and transplanted kidney grafts. It starts in kidney glomeruli. In the early stage of FSGS, it mainly targets the visceral epithelium (also called podocytes) that comprise cells with foot processes to regulate functioning of the renal filtration barrier. Generally, effacement of podocyte foot processes marks the first ultrastructural step that is associated with loss of plasma proteins into the urine. While gene defects in podocytes have been identified for hereditary FSGS, there are also cases that occur in the absence of gene defects or with post-transplant recurrence in about 30% of patients receiving a kidney graft. These observations led to the suggestion that development of FSGS can be associated with a "FSGS permeability factor" in the patient's circulation (see Savin et al., Translational Res. 151:288-292, 2008). Both Staphylococcus protein A and galactose have high affinity for FSGS permeability factor. Ex vivo removal from the body of a subject by plasmapheresis or binding to staphylococcal protein A improved proteinuria in FSGS patients. When a patient with a nephrotic syndrome resistant to corticosteroids, immunosuppression, and plasmapheresis was administered oral galactose, his nephrotic syndrome went into remission for more than two years (De Smet et al., Nephrol. Dial. Transplant. 24:2938-2940, 2009). This led to the hypothesis that interactions between FSGS permeability factor in the circulation and galactose moieties on the glomerular glycocalyx might induce a nephrotic syndrome.

But in another case, there was no improvement of proteinuria when a dialysis-dependent patient was administered galactose (Savin et al., 2008). Plasmapheresis appears to have improved proteinuria only for a short time and required early intervention. Furthermore, molecular identification of FSGS permeability factor was uncertain because the equal effectiveness of its removal by protein A and ovine anti-human immunoglobulin, which implied the factor included an immunoglobulin determinant, appeared to contradict the determination of a molecular weight smaller than 100 kDa by size fractionation (Dantal et al., 3. Am. Soc. Nephrol. 9:1709-1715, 1998).

WO 2010/054189 disclosed a role for suPAR in pathogenesis of proteinuric kidney disease. But it did not disclose ex vivo removal of suPAR by an extracorporeal process as therapy and/or prevention of kidney disease. For the present invention, neutralizing antibodies are not necessarily needed.

Dantal et al. (1998) taught away from extracorporeal removal of FSGS permeability factor using an immunoaffinity cartridge by warning, "Plasma immunoadsorption on columns containing sheep anti-human immunoglobulins or protein A does not offer a realistic approach for treating FSGS patients because of its transient effect and its cost" (page 1715). Therefore, a longer lasting and less expensive technology to improve proteinuria and/or to avoid kidney failure was needed.

In a multi-center study, the concentration of suPAR has now been determined in sera collected from patients having glomerular disease. suPAR is significantly elevated in FSGS patients, and is found to possess characteristics of an FSGS permeability factor. The suPAR can now be removed from the circulation of a subject needing treatment to provide desirable therapy for kidney disease and/or its prevention.

SUMMARY

It is an objective to remove circulating soluble urokinase receptor (suPAR) as at least therapy for kidney disease or its prevention.

In one embodiment, an immunosorbent cartridge specific for suPAR is provided. The cartridge comprises: (i) an inlet; (ii) a support, which may be a solid matrix; (iii) one or more suPAR-specific antibodies or functional portions thereof that are attached to the support before, during, and/or after specifically binding thereto of suPAR; (iv) an outlet; (v) a housing that contains the support therein; and (vi) a fluid path through the housing that connects the inlet and the outlet. suPAR in a fluid phase, comprising soluble blood components, enters at the inlet, follows the fluid path through the housing, and exits at the outlet. suPAR binds to the antibodies or functional portions thereof in an immune complex. The complex may be immobilized to the support through the antibodies or functional portions thereof. Antibodies or functional portions thereof may be either reversibly or irreversibly attached to the support. The cartridge may be able to bind from about 2 μg to about 10 μg of suPAR. The support may be at least one fluid-permeable membrane, one or more porous fiber(s), or a plurality of particles. The housing may be configured for separation by membrane filtration or column chromatography. Aseptic packaging surrounds the housing to maintain it, the inlet, and the outlet in sterile and pyrogen-free conditions.

Another embodiment is use of an immunosorbent cartridge to reduce the amount or the concentration of suPAR circulating in the blood of a subject. Reduction is measured by comparing the level of suPAR before and after such treatment.

A further embodiment is removing suPAR from the circulation of a subject (e.g., ex vivo). A fluid phase, which is comprised of suPAR and other plasma proteins (e.g., albumin and/or immunoglobulins), is contacted with one or more suPAR-specific antibodies or functional portions thereof under binding conditions. Most of the circulating suPAR may be bound in immune complexes selectively in preference to the other plasma proteins in the fluid phase. Immune complexes, which are comprised of suPAR bound to the antibodies or functional portions thereof, are separated from the other plasma proteins not complexed in the fluid phase. At least some of the other plasma proteins in the fluid phase, separately or together with substantially all blood cells, are then returned to the circulation of the subject. The complex may be immobilized on a support before the separation step. In blood obtained from the subject, plasma proteins may be substantially separated from blood cells (e.g., erythrocytes, leukocytes, and thrombocytes) after the contacting step, before the contacting step, before the separation step, or after the contacting step and before the separation step. One or more anti-coagulant(s) (e.g., heparin, citrate, oxalate, EDTA) may be added to the fluid phase. Separation of complex from other plasma proteins may be performed by membrane filtration or column chromatography. Plasma suPAR may be removed from the circulation in from ten to 20 rounds of binding between a fluid phase and one or more suPAR-specific antibodies or functional portions thereof followed by separation from at least some of the other plasma proteins. In a single round, from at least about 20% to at least about 30% of circulating suPAR may be removed from the subject. The fluid phase may be maintained under sterile and pyrogen-free conditions.

In yet another embodiment, risk for FSGS or its recurrence is assessed in a subject. A fluid phase containing plasma proteins is obtained from a subject. The fluid phase is contacted with an in vitro culture of human differentiated podocytes. After induction by one or more of the plasma protein(s), β3 integrin activity on the podocytes is determined. For a plasma protein that increases β3 integrin activity, at least an altered level of the plasma protein or a mutation in the plasma protein is a risk factor for FSGS or its recurrence in the subject. The risk factor may be suPAR.

A yet additional embodiment is monitoring soluble urokinase receptor (suPAR) during its removal from a subject. A sample is taken from the circulation of a subject before removal, suPAR is removed from the circulation of the same subject, and another sample is taken from the circulation of the subject after removal. suPAR is measured in the samples, which can be converted to measurements of suPAR in the blood depending on the source of the sample, and compared. Comparison of the measurements before and after removal should show a reduction of the amount or the concentration of circulating suPAR in the subject. The reduced concentration may be equivalent to less than about 3.0 ng/ml of blood, less than about 2.5 ng/ml of blood, less than about 2.0 ng/ml of blood, less than about 1.5 ng/ml blood, or less than about 1.0 ng/ml blood in the circulation of a subject.

Human plasma or blood, which is outside the body, is provided. It is depleted of soluble urokinase receptor (suPAR) to a concentration of less than 1 ng/ml.

Novel fragments of soluble urokinase receptor (suPAR) are provided. One or more of them have a molecular weight from about 22 kDa to about 45 kDa. Their presence is associated with occurrence of focal segmental glomerulosclerosis (FSGS).

Further objectives will be apparent to a person skilled in the art from the following description and claims, and generalizations thereto.

DESCRIPTION OF DRAWINGS

FIG. 3 lists pathology score for kidneys exposed to wild-type suPAR or E134A mutant. The histopathological alteration of the kidneys is semi-quantitatively scored as an integer value from 0 to 4. The morphology of kidneys that were exposed to the E134A mutant is normal. In contrast, multiple abnormalities of kidney phenotypes are observed in wild-type suPAR-overexpressing mice. Hematoxylin and eosin (H&E) and Periodic Acid Schiff (PAS) staining revealed pathological features such as glomerular tuft adhesion, hypercellularity, hyperlobulation, and mesangiolysis.

FIG. 4 lists pathology score for kidneys exposed to wild-type suPAR and treated with uPAR blocking antibody (Mab) every two days up to four weeks; control mice received the same amount of isotype IgG (Con) (n=4 for each group). The histopathological alteration of the kidneys is semi-quantitatively scored as an integer value from 0 to 4. Hematoxylin and eosin (H&E) and Periodic Acid Schiff (PAS) staining indicate there is no overt renal injury with the suPAR engineered mice which received anti-uPAR antibody. In contrast, the mice that received isotype IgG show significant kidney damages reminiscent of FSGS at early phase, similar to that observed with the wild-type suPAR engineered mice.

FIG. 5 lists distribution of age (years) and sex for study population.

FIG. 6 lists P values from multiple regression analysis of suPAR in FSGS-CT cohort.

FIG. 7 lists baseline characteristics of patients in FSGS-CT cohort after treatment. Patients were randomly assigned to either the cyclosporine (CSA) or the combination of dexamethasone/mycophenolate mofetil (MMF) arm.

FIG. 8 lists baseline characteristics of PodoNet cohort by etiology. FSGS patients are divided into genetic/familial (Gen/Fam) and Non-Genetic subgroups.

FIG. 9 lists baseline characteristics of PodoNet cohort by treatment: FSGS patients treated with mycophenolate mofetil (MMF) and others.

DESCRIPTION OF SPECIFIC EMBODIMENTS

Figures 1, 2:
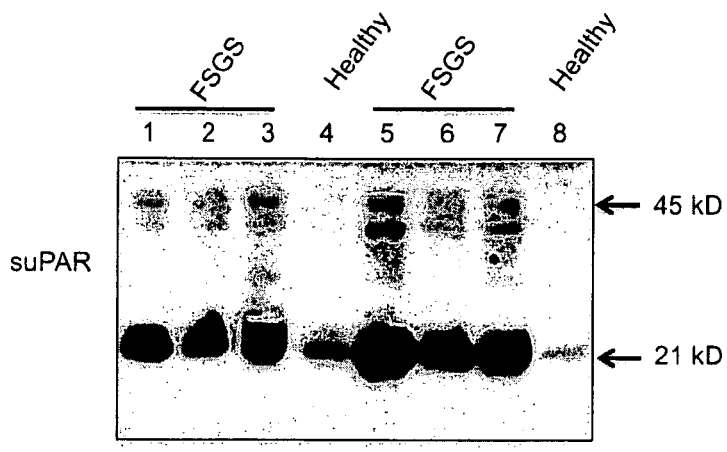
FIG. 1 shows suPAR exists in multiple forms in FSGS serum and is largely not albumin bound. To examine suPAR in sera of FSGS patients, immunoprecipitation was performed by incubating a monoclonal anti-uPAR antibody with FSGS sera, followed by immunoblotting with a polyclonal anti-uPAR antibody. While a major band was observed at about 22 kDa, two other weaker bands at about 40 kDa and 45 kDa were also found.
FIG. 2 lists percentages of active β3 integrin (AP5 staining) glomeruli in healthy (Control), primary or recurrent focal segmental glomerulosclerosis (FSGS), minimal change disease (MCD), and membranous nephropathy (MN). P<0.05 for Primary FSGS vs. Control; P<0.01 for Recurrent FSGS vs. Control.

Plasma is the liquid component of whole blood, containing: dissolved proteins, lipids, and carbohydrates; suspended cells such as erythrocytes, leukocytes, and thrombocytes; ions and other small molecules; and other soluble components. Serum is plasma without fibrinogen and other clotting factors.

Blood, preferably containing an anti-coagulant, can be separated by centrifugation into a fluid phase (e.g., plasma) and blood cells. Protein components of blood include albumin, immunoglobulins, lipoproteins, and clotting factors (e.g., fibrinogen). Soluble urokinase receptor (suPAR) is contained in a fluid phase of blood, plasma, serum, urine, or their equivalent. For example, the fluid phase may be a sample containing blood, plasma, serum, urine, or their equivalent, which may be diluted or concentrated prior to processing. Thus, the equivalent level of suPAR in blood may need to be multiplied or divided from its level in a sample using a factor of dilution or concentration, respectively. It is preferred that suPAR is removed selectively by a degree of at least ten times as compared to one or more blood protein(s) such as albumin, immunoglobulins, lipoproteins, and clotting factors. For example, in blood, a normal physiological level of suPAR may be less than about 3 ng/ml, which is related to the age of a human patient, and the cutoff for "normal" may increase in the elderly.

Urokinase receptor (uPAR) is a glycosylphosphatidylinisotol (GPI)-anchored protein, which has been identified as cellular receptor for urokinase and is also a versatile signaling orchestrator through association with other membrane receptors, including integrins and matrix molecules. uPAR has three domains DI, DII and DIII as numbered from the amino terminus to the carboxyl terminus of the polypeptide. It is released from the cell's plasma membrane by cleavage of the GPI anchor and can be found as suPAR in biological fluids. suPAR can be further cleaved in the linker between domains DI and DII, thereby releasing for example the fragment DI, DII or DIIDIII. Thus, suPAR can range in molecular weight from 20 kDa to 50 kDa in the circulation depending on the degree of glycosylation and proteolysis. Here, ex vivo removal of suPAR from the circulation of a subject can be an effective therapeutic and/or preventive treatment for proteinuria, kidney disease, glomerular disease, kidney failure, kidney graft rejection, or a combination thereof. This is distinct from administration in vivo of antibodies or functional portions thereof to a subject to neutralize circulating suPAR.

In one embodiment, an immunosorbent cartridge specific for circulating suPAR is provided. The cartridge is comprised of an inlet; a support, which may be a solid matrix; one or more suPAR-specific antibodies or functional portions thereof that are attached to the support before, during, and/or after specifically binding thereto of suPAR; an outlet; a housing that contains the support therein; and a fluid path through the housing that connects the inlet and the outlet. suPAR in a fluid phase, comprising soluble blood components, enters at the inlet, follows the fluid path through the housing, and exits at the outlet. Blood cells are preferably not passaged through the cartridge; thus, they may be separated from soluble blood components and follow an alternative path that bypasses the cartridge. The suPAR binds to the antibodies or functional portions thereof in an immune complex, and the complex may be immobilized to the support. The cartridge may be able to bind from about 1 μg to about 30 μg of suPAR, from about 2 μg to about 10 μg of suPAR, from about 10 μg to about 20 μg of suPAR, or any combination thereof. The support may be at least one fluid-permeable membrane, one or more porous fiber(s), or a plurality of particles. Antibodies or functional portions thereof may be either reversibly or irreversibly attached to the support. The housing may be configured for separation by membrane filtration or column chromatography. Aseptic packaging surrounds the housing to maintain it, the inlet, and the outlet in sterile and pyrogen-free conditions.

In another embodiment, circulating suPAR is removed from a subject ex vivo and separated from other plasma proteins (e.g., albumin and/or immunoglobulins), wherein at least some of the other plasma proteins are returned in a fluid phase. A fluid phase, which is comprised of suPAR and other plasma proteins, is contacted with one or more suPAR-specific antibodies or functional portions thereof under binding conditions. Most of the suPAR is bound in immune complexes selectively in preference to the other plasma proteins in the fluid phase. Blood cells are preferably separated from soluble blood components. Immune complexes, which are comprised of suPAR bound to the antibodies or functional portions thereof, are separated from the other plasma proteins not complexed in the fluid phase. Separation may be in heterogeneous or homogeneous format. At least some of the other plasma proteins in the fluid phase, separately or together with substantially all blood cells, are then returned to the circulation of the subject. The complex may be immobilized on a support before the separation step. In blood obtained from the subject, plasma proteins may be substantially separated from blood cells (e.g., erythrocytes, leukocytes, and thrombocytes) after the contacting step, before the contacting step, before the separation step, or after the contacting step and before the separation step. Optionally, one or more anti-coagulant(s) (e.g., heparin, citrate, oxalate, EDTA) may be added to the fluid phase. Separation may be performed by membrane filtration or column chromatography. Plasma suPAR may be removed from the circulation in from two to 50 rounds, from five to ten rounds, from ten to 20 rounds, from 20 to 30 rounds, or any combination thereof between a fluid phase and one or more suPAR-specific antibodies or functional portions thereof followed by separation from at least some of the other plasma proteins. In a single round, at least about 10% of circulating suPAR, at least about 20% of circulating suPAR, at least about 30% of circulating suPAR, at least about 40% of circulating suPAR, at least about 50% of circulating suPAR, or any range therebetween (e.g., from about 10% to about 20%, from about 20% to about 30%, from about 30% to about 40%, from about 40% to about 50%, or any combination thereof) may be removed from the circulation. The fluid phase may be maintained under sterile and pyrogen-free conditions.

Specific binding between circulating suPAR and the antibodies or functional portions thereof forms an immune complex. The complex immobilized on the support may remove suPAR from the circulation. The cartridge is preferably adapted for use in apheresis and inserted into an apparatus appropriate thereto. During apheresis, blood may be initially taken out of the body through a needle or previously implanted catheter. Plasma may be separated from cells in blood using a separator: e.g., discontinuous flow centrifugation, continuous flow centrifugation, or size-selective filtration. Removal of suPAR is preferably an extracorporeal process relative to the subject's body, wherein at least some of the plasma proteins other than suPAR, separately or together with substantially all blood cells, are returned thereto.

Immobilized suPAR may be separated from at least some of the other plasma proteins (e.g., albumin and/or immunoglobulins) in the fluid phase. Cartridge parts (e.g., inlet, outlet, and housing) may be manufactured from glass, polypropylene, polystyrene, or stainless steel. The support may be formed separately from the housing or as an integral part thereof. At least one fluid-permeable membrane, one or more porous fiber(s), and a plurality of particles are examples of the support, which may be manufactured from agarose, alumina, cellulose, dextran, polyacrylamide, polyacrylate, polyamide, and silica. An external pump may provide line pressure through flexible tubing to the cartridge and, thereby, control the flow rate of a fluid phase through a membrane or a column. Blood may be taken from a subject's circulation, processed extracorporeally (i.e., plasma proteins and cells separated, then suPAR removed from plasma proteins), and the remainder of plasma proteins and blood cells returned separately or together to the subject's circulation.

Specificity of a binding agent (e.g., antibody, aptamer, peptide, uPAR ligand such as uPA) for suPAR can be confirmed by comparison to non-specific binding of the binding agent to another plasma protein (preferably non-carrier protein having chemical characteristics and abundance similar to suPAR). The binding agent may recognize an epitope of suPAR, which may or may not be involved in the interaction with integrin β3. Binding between suPAR and the antibodies or functional portions thereof, then optional washing, attaching, and separating steps (in any order) are performed under appropriate conditions of ionic strength, solvent, pH, pressure, temperature, flow rate, etc. For example, the fluid phase may be further comprised of salts (ionic strength), aqueous carrier (solvent), and buffer (pH). Binding and/or attaching may be improved by increasing incubation time, blocking non-specific interactions, binding in solution prior to attachment to solid matrix, passaging the fluid phase repetitively through the support (e.g., from two to 50 times, from five to ten times, from ten to 20 times, from 20 to 30 times, or any combination thereof), regenerating the cartridge by elution of bound suPAR from antibodies or functional portions thereof between rounds, or any combination thereof. At least about 10% of circulating suPAR, at least about 20% of circulating suPAR, at least about 30% of circulating suPAR, at least about 40% of circulating suPAR, at least about 50% of circulating suPAR, or any range therebetween (e.g., from about 10% to about 20%, from about 20% to about 30%, from about 30% to about 40%, from about 40% to about 50%, or any combination thereof) may be removed each time. For effective treatment, suPAR may be reduced to a concentration equivalent to less than about 3.0 ng/ml of blood, less than about 2.5 ng/ml of blood, less than about 2.0 ng/ml of blood, less than about 1.5 ng/ml blood, or less than about 1.0 ng/ml in the circulation of a subject.

The subject may be a human or another mammal. A subject afflicted with at least focal segmental glomerulosclerosis (FSGS), a glomerular disease, a disorder characterized by proteinuria, end-stage kidney disease, or symptoms thereof; who might reject a kidney graft or is at risk of graft rejection, and those having a native kidney undergoing failure may be in need of treatment. Optionally, a subset of patients (e.g., having the Leu33Pro polymorphism in the human integrin β3 gene, heterozygous and/or homozygous; the equivalent to at least about 3 ng suPAR per ml blood in the circulation; or both) may be selected for treatment.

suPAR may be reduced to a level equivalent to less than about 3.0 ng/ml of blood, less than about 2.5 ng/ml of blood, less than about 2.0 ng/ml of blood, less than about 1.5 ng/ml blood, less than about 1.0 ng/ml blood in the circulation of a subject, or any range therebetween (e.g., from about 3.0 ng/ml to about 2.0 ng/ml of blood, from about 2.0 ng/ml to about 1.0 ng/ml of blood, or their equivalents).

An immunosorbent cartridge, which is specific for suPAR relative to other soluble proteins in the blood, may be used to remove suPAR from the circulation of a subject. Alternatively, the immunosorbent cartridge may be used to reduce the amount or the concentration of suPAR circulating in the blood of a subject. Reduction may be measured by comparing the level of suPAR before and after treatment.

Risk for FSGS or its recurrence may be assessed in a subject. A fluid phase containing plasma proteins is obtained from a subject. The fluid phase is contacted with an in vitro culture of human differentiated podocytes. After induction by one or more of the plasma protein(s), β3 integrin activity on the podocytes is determined. For a plasma protein that increases β3 integrin activity, at least an altered level of the plasma protein or a mutation in the plasma protein is a risk factor for FSGS or its recurrence in the subject. The risk factor may be suPAR.

A yet additional embodiment is monitoring soluble urokinase receptor (suPAR) during its removal from a subject. A sample is taken from the circulation of a subject before removal, suPAR is removed from the circulation of the same subject, and another sample is taken from the circulation of the subject after removal. suPAR is measured in the samples, which can be converted to measurements of suPAR in the blood depending on the source of the sample, and compared. Comparison of the measurements before and after removal should show a reduction of the amount or the concentration of circulating suPAR in the subject. The reduced concentration may be equivalent to less than about 3.0 ng/ml of blood, less than about 2.5 ng/ml of blood, less than about 2.0 ng/ml of blood, less than about 1.5 ng/ml blood, or less than about 1.0 ng/ml blood in the circulation of a subject.

Alternatively, a sample may be taken from the circulation of a subject prior to and/or subsequent to kidney transplantation. The kidney is not transplanted or risk of kidney disease recurrence is decreased by removing suPAR from the circulation. In a first alternative, a sample is taken prior to transplantation and a kidney may be transplanted when the level of suPAR in the circulation of the same subject is below a pre-determined cutoff level (e.g., equivalent to less than about 3.0 ng/ml of blood, less than about 2.5 ng/ml of blood, less than about 2.0 ng/ml of blood, less than about 1.5 ng/ml blood, less than about 1.0 ng/ml blood, or any range therebetween such as from about 3.0 ng/ml to about 2.0 ng/ml of blood, from about 2.0 ng/ml to about 1.0 ng/ml of blood, or their equivalents). In a second alternative, a sample is taken subsequent to transplantation (e.g., at intervals of at least every week, at least every two weeks, at least every four weeks, at least every six weeks, or at least every eight weeks) and the level of suPAR in the circulation of the same subject is maintained below a pre-determined cutoff level (e.g., equivalent to less than about 3.0 ng/ml of blood, less than about 2.5 ng/ml of blood, less than about 2.0 ng/ml of blood, less than about 1.5 ng/ml of blood, less than about 1.0 ng/ml blood, or any range therebetween such as from about 3.0 ng/ml to about 2.0 ng/ml of blood, from about 2.0 ng/ml to about 1.0 ng/ml of blood, or their equivalents). In a third alternative, samples are taken both prior and subsequent to kidney transplantation as in the foregoing. In the three alternatives, if the level of suPAR is above the cutoff level, then suPAR may be removed from the circulation of the subject.

Removal of circulating suPAR may be combined with one or more of immunosuppressive treatment (e.g., corticosteroids with or without cyclophosphamide, cyclosporine, mycophenolates, and/or rituximab); blocking renin-angiotensin system, calcium channel blockers, beta blockers, and diuretics; and lowering lipids. Conversely, because adjunctive treatment is not necessarily required, only removal of circulating suPAR may be effective and there may be a proviso not to use one or more of immunosuppressive, antihypertension, and lipid-lowering treatment(s).

In vivo administration of antibodies or functional portions thereof specific for suPAR and/or plasmapheresis (i.e., limited dilution of all plasma proteins) may be avoided by use of the above-described methods. Thus, there may be a proviso not to use such treatments together with removal of circulating suPAR.

The terminology used to describe specific embodiments is not intended to be limiting of the invention. As used herein, singular forms such as "a" and "an" and "the" are intended to be construed as "at least one" and to include plural forms such as "more than one" and "plurality" unless context clearly indicates otherwise. Further, to the extent that the terms "including" and "includes" and "having" and "has" and "with" or variants thereof are used in the specification and claims, such terms are intended to be inclusive in a manner similar to the definition of "comprising" herein.

The term "about" means within an acceptable error range for the particular value as determined by a person skilled in the art, which will depend in part on how the value is determined or quantitated, i.e., limitations of the measurement system. For example, the term can mean within one or more than one standard deviation per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold of a given value. Where particular values are described in the specification and claims, unless otherwise stated, the term "about" meaning within an acceptable error range for the particular value should be assumed.

As used herein, "proteinuria" refers to proteins passing through podocytes that have suffered damage or through a podocyte-mediated barrier that normally would not allow protein passage. Such structural damage may be visualized in vitro or in vivo. In the body of a subject, "proteinuria" may refer to the presence of an excessive amount of serum protein (e.g., albumin) in urine. Proteinuria may be a symptom of renal, urinary, and nephrotic syndromes (i.e., proteinuria larger than 3.5 grams per day), eclampsia, toxic lesions of kidneys, pancreatic distress, and it is frequently a symptom of diabetes mellitus. With severe proteinuria, general hypoproteinemia can develop and it results in diminished oncotic pressure (ascites, edema, hydrothorax).

The term "specific" of "specifically" in the context of antibody binding refers to a bimolecular interaction between a functional (i.e., antigen-binding) portion of the antibody and a cognate portion of the antigen that selects for suPAR (e.g., DII, DIII, an epitope that may or may not be involved in the interaction with integrin $\beta 3$) in the presence of a mixture of other serum proteins (e.g., albumin). Here, the antibody or functional portion thereof may not necessarily neutralize integrin $\beta 3$ activation and foot process effacement in podocytes. Preferably, an epitope of suPAR accessible in the circulation is bound. Under reaction conditions appropriate for binding, the antibody or functional portion thereof binds to suPAR and does not bind significantly to another serum protein (e.g., albumin) that might be present. Specificity of antibody or functional portion thereof for suPAR is greater than protein A or a lectin for an FSGS permeability factor. Specific binding of suPAR may take place in solution or on a substrate. The reaction format requires separation of bound protein from other serum proteins (e.g., albumin) to remove suPAR from the circulation of the subject. But immobilization of an immune complex containing suPAR is not necessarily required for separation because both homogeneous and heterogeneous formats are possible alternatives for processing.

Removal may be monitored with a detectable signal associated with binding of suPAR. Detectable signals may be direct or indirect, attached to any part of a bound complex, measured competitively, amplified, or combinations thereof. A blocking or washing step may be interposed to improve sensitivity and/or specificity. The attachment of antibody or suPAR to a substrate before, after, or during binding results in capture of a previously unattached species. Such immobilization (i.e., reversible or irreversible attachment) will be stably attached to the substrate under washing conditions. Detection techniques include antibody binding (e.g., ELISA or RIA), magnetic resonance, mass spectroscopy, electron microscopy of cell ultrastructure, and/or fluorescent labeling or histochemical staining of cells and tissues with or without separation by biochemical fractionation, gel electrophoresis, and/or liquid chromatography.

Here, "a subject in need of treatment" refers to a subject, including a human or other mammal, who is affected with a disorder characterized by proteinuria, is at risk for or is undergoing kidney failure, has received a kidney graft, or any combination thereof. A disorder characterized by proteinuria includes, for example, kidney or glomerular diseases, membranous glomerulonephritis, focal segmental glomerulonephritis, minimal change disease, nephrotic syndromes, pre-eclampsia, eclampsia, kidney lesions, collagen vascular diseases, stress, strenuous exercise, benign orthostatic (postural) proteinuria, focal segmental glomerulosclerosis, IgA nephropathy, IgM nephropathy, membranoproliferative glomerulonephritis, membranous nephropathy, end-stage kidney disease, sarcoidosis, Alport's syndrome, diabetes mellitus, kidney damage due to drugs, Fabry's disease, infections, aminoaciduria, Fanconi syndrome, hypertensive nephrosclerosis, interstitial nephritis, sickle cell disease, hemoglobinuria, multiple myeloma, myoglobinuria, cancer, Wegener's granulomatosis, and glycogen storage disease type 1. A "subject in need of treatment" may be affected by one or more of the foregoing disorders, may be a heterozygote for the polymerphism Leu33Pro in the human integrin $\beta 3$ gene, may be a homozygote for the polymorphism Leu33Pro in the human integrin $\beta 3$ gene, may have at least about 3 ng suPAR per ml blood in the circulation, or any combination thereof.

As defined herein, "an effective amount" is a quantity of specific binding agent sufficient to produce a therapeutic or preventive result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age (e.g., at least about 40 years, at least about 45 years, at least about 50 years, at least about 55 years, at least about 60 years) of the subject, and other diseases present. Moreover, treatment of a subject with a therapeutically effective amount of the compounds of the invention can include a single treatment or a series of treatments. For effective treatment, suPAR may be reduced to a concentration equivalent to less than about 3.0 ng/ml of blood, less than about 2.5 ng/ml of blood, less than about 2.0 ng/ml of blood, less than about 1.5 ng/ml blood, or less than about 1.0 ng/ml in the circulation of a subject.

Urokinase receptor (uPAR) includes the membrane-bound protein, precursors, mutants, functional variants, any isoforms or analogs, etc. particularly from human or homologs from other mammals. Soluble forms thereof are known as soluble uPAR. The terms "active" and "activity" in regard to soluble uPAR refers to a soluble portion of uPAR that has a biological or an immunological function of native uPAR. As used herein, "biologic" and "biological" refers to a function corresponding to a natural activity of suPAR such as its involvement in signaling pathways, activation of $\beta 3$ integrin, foot process effacement, inducing proteinuria, or any combination thereof.

As used herein, the term "variant" may encompass an amino acid sequence related to wild-type suPAR. This definition may include, for example, an allelic, splice, or polymorphic variant. A species variant is a homolog that varies between different species. A "variant" may also result from one or more mutations in the amino acid sequence such as substitutions, insertions, deletions, duplicated domains, and shuffled domains whose function may or may not be altered. Each of these alterations may occur alone, or in combination with the others, one or more times in a given amino acid sequence. A "functional" variant has at least one biological activity of suPAR such as activation of β3 integrin, foot process effacement, inducing proteinuria, or any combination thereof.

As used herein, the term "fragment" is a portion of the amino acid sequence of suPAR or a variant thereof. A "fragment" may be at least about ten contiguous amino acid residues, at least about 20 contiguous amino acid residues, at least about 30 contiguous amino acid residues, at least about 40 contiguous amino acid residues, at least about 50 contiguous amino acid residues, at least about 60 contiguous amino acid residues, at least about 70 contiguous amino acid residues, 80 contiguous amino acid residues, at least about 90 contiguous amino acid residues, at least about 100 contiguous amino acid residues, at least about 120 contiguous amino acid residues, at least about 140 contiguous amino acid residues, 160 contiguous amino acid residues, at least about 180 contiguous amino acid residues, at least about 270 contiguous amino acid residues in length, or any range or integer therein. The "fragment" is shorter than the about 280 residues of the full-length amino acid sequence of suPAR. "Overlapping fragments" as used herein refer to contiguous peptide fragments that begin towards the amino terminus and end towards the carboxyl terminus of suPAR. An "overlapping fragment" shares from one to five contiguous amino acid residues, at least about three contiguous amino acid residues, or at least about ten contiguous amino acid residues with the next peptide fragment.

As used herein, a "derivative" is a modification, for example, by glycosylation, pegylation, phosphorylation, sulfation, reduction/alkylation, acylation, chemical coupling, or mild formalin treatment of suPAR or a variant thereof. Alternatively, a "derivative" may be modified to contain a detectable label, either directly or indirectly, including, but not limited to, a radioisotope, fluorescent, spin, or enzyme label.

Antibodies or functional portions thereof specific for suPAR are known. They can be used for binding, removing, or detecting. Polyclonal or monoclonal antibodies are obtained by immunizing animals (e.g., chicken, hamster, mouse, rat, rabbit, goat, horse) with an antigen related to suPAR, and optionally affinity purified against the same antigen or cognate epitope. Antigen may be native suPAR, a fragment thereof produced by enzyme proteolysis or genetic engineering, fusion polypeptide containing an suPAR epitope, or in vitro translated or synthesized polypeptide that contains at least one or more suPAR epitopes bound by an antibody. Thus, antibodies originally generated against uPAR, domain DII and/or DIII, or a fragment thereof may be tested for specificity against native suPAR. Antibodies may be selected for those that bind suPAR in the circulation, but do not neutralize integrin in activation and foot process effacement. Functional portions of antibody may be fragments prepared by enzyme proteolysis or genetic engineering; humanized antibody and single-chain antibody may be prepared by transplanting hypervariable regions from the antigen binding site of an antibody to a framework responsible for overall conformation. Other types of binding agents (e.g., aptamer, peptide, uPAR ligand such as uPA) may be obtained by screening a combinatorial library for a member that specifically binds antigen (e.g., phage display library). The antigen to generate specific anti-suPAR antibodies or functional portions thereof may be a full-length uPAR or any fragment thereof (see above definition). Antibodies or functional portions thereof specifically binding to suPAR have low or non-detectable binding to other plasma proteins. Functional portions of suPAR-specific antibodies are defined by incorporating the above definitions of variant, activity, functional, fragment, and derivative. Cells, which include hybridomas, may be used to produce these antibodies or functional portions thereof.

Antibodies specifically bind to suPAR with high affinity (Kd). For example, a human, rabbit, mouse, chimeric, or humanized antibody may be able to bind suPAR with a Kd less than $10^{-5}$, less than $10^{-6}$, less than $10^{-7}$, less than $10^{-8}$, less than $10^{-9}$, less than $10^{-10}$, less than $10^{-11}$ M, or any range or value therein. Affinity and/or avidity measurements can be measured by KinExA™ and/or BIACORE™ apparatus.

It will be appreciated that specific embodiments are not limited to a particular form of antibodies (cf. functional portions thereof) or a particular method for generating and obtaining them. For example, anti-suPAR antibodies or functional portions thereof may be a full-length antibody (e.g., having an intact human Fc region) or an antibody fragment (e.g., a Fab, Fab', F(ab')$_2$, Fv or Dab). Dabs are small functional portions of human antibodies. Monoclonal antibodies may be produced in hybridoma that secrete them. Functional portions thereof may be proteolytically cleaved antibodies or produced in a recombinant cell transfected with a gene expression cassette encoding an antibody fragment.

Proteinuria can be primarily caused by one or more alterations of structural proteins involved in the cellular mechanism of filtration. The pathophysiological causes of proteinuria can be divided in the following major groups: (1) genetically determined disturbances of the structures which form the "glomerular filtration unit" like the glomerular basement membrane, the podocytes, or the slit diaphragm; (2) inflammatory processes, either caused directly by autoimmune processes or induced indirectly by microbes; (3) damage of the glomeruli caused by agents; or (4) as the final result of progressive tubulointerstitial injury finally resulting in the loss of function of the entire nephron.

Example 1

Increased suPAR in Sera from FSGS Patients

Soluble urokinase receptor (suPAR) was measured by ELISA in sera of patients with glomerular disease. For transplant patients, suPAR levels were measured from pre-transplantation sera unless otherwise indicated. suPAR serum levels were found to be significantly elevated in FSGS patients when compared to healthy subjects. In contrast, any significant variance of suPAR was lacking in patients with minimal change disease (MCD), whether in relapse (RLP) or remission (REM), membranous nephropathy (MN), or pre-eclampsia. $P<0.05$ for FSGS vs. MN or pre-eclampsia respectively; $P<0.001$ for FSGS vs. Healthy, MCD RLP, MCD or REM respectively. FSGS was then stratified into three different subpopulations: primary FSGS, recurrent FSGS in the allograft and FSGS without recurrence after transplantation. Significantly higher levels of serum suPAR were identified in the pre-transplant sera of patients later developing recurrent FSGS compared to those transplant patients without recurrence. $P<0.01$ for Recurrent FSGS vs. Non-recurrent FSGS or Non-transplant primary FSGS respectively.

A longitudinal study was performed to evaluate the levels of serum suPAR in recurrent and non-recurrent FSGS patients from their pre-transplantation blood draw up to one year post-transplantation. Significantly higher suPAR levels were found in recurrent FSGS patients at one year post-transplantation (P<0.001 for Recurrent FSGS vs. Non-recurrent FSGS), indicating that patients who were predicted and developed FSGS recurrence maintain higher one-year post-transplantation suPAR levels in comparison to those FSGS patients without recurrence. Moreover, when comparing pre-transplantation levels to post-transplantation (6-12 months) levels, serum suPAR further increased in eight of 13 recurrent FSGS patients, but not in non-recurrent FSGS patients. The size of variance was analyzed and suPAR was found at 3000 pg/ml or above in 45 out of 63 FSGS patients, but only in four out of 11 MN patients, one out of seven pre-eclampsia patients, and in none of 25 MCD patients (Table 1).

TABLE 1 suPAR Levels

| | FSGS | MCD | MN | PE | P value* |
|---|---|---|---|---|---|
| suPAR ≥3000 pg/ml | 45 | 0 | 4 | 1 | |
| suPAR <3000 pg/ml | 18 | 25 | 7 | 6 | P < 0.0000 |

*Fisher's exact test for FSGS versus other groups as a whole

While suPAR levels correlate to presence of proteinuria, there was no correlation between pre-transplantation serum suPAR levels and the degree of proteinuria after transplantation (Pearson r=0.16, P=0.50). Moreover, suPAR levels do not correlate to estimated glomerular filtration rate (eGFR), either in pre-transplantation sera (eGFR<15) (Pearson r=0.36, P=0.16) or post-transplantation sera (eGFR>60 on average) (Pearson r=0.10, P=0.58). No significant difference of eGFR was found between recurrent FSGS and non-recurrent FSGS, either before or after transplantation (i.e., from one month up to one year after transplantation). These findings also suggest that pre-transplantation high serum level of suPAR is associated with post-transplantation FSGS recurrence. In summary, these data show that suPAR is specifically increased in FSGS but not in other analyzed glomerular diseases with podocyte involvement such as MCD and MN, nor in pre-eclampsia, a proteinuric disease largely caused by endothelial dysfunction.

Since multiple forms of suPAR have been reported due to domain cleavage or alternative splicing, the forms of suPAR existing in the blood of FSGS patients were identified. FSGS sera were immunoprecipitated with anti-uPAR antibody. A predominant suPAR fragment was found at about 22 kDa, along with two other forms at about 45 and about 40 kDa, albeit at much lower expression levels (FIG. 1). In contrast, healthy subjects do not show strong expression of suPAR in their sera. It was next determined whether suPAR is albumin bound or freely circulating in the blood. To define whether serum suPAR is bound to albumin, FSGS sera were immunoprecipitated with a specific human albumin antibody. The precipitates were then blotted with antiadiponectin antibody as well as anti-uPAR antibody. While adiponectin (an albumin-bound protein) could be detected, suPAR was not detected. Moreover, immunoprecipitation of FSGS sera with a monoclonal anti-uPAR antibody followed by immunoblotting with a human albumin antibody did not detect albumin in the precipitants, suggesting that suPAR in the blood of FSGS patients is largely not albumin bound. As a control, stripping albumin antibody off the Western blot and reblotting with anti-uPAR antibody indicates the presence of uPAR in the precipitates.

As a ligand of uPAR, urokinase (uPA) levels are often found to be elevated in cancer patients with higher suPAR levels. Thus, serum uPA levels were measured in our glomerular disease cohort as well. Interestingly, unlike serum suPAR, there was no difference in serum uPA levels observed among the groups: Healthy, MCD RLP, MCD REM, Primary, Recurrent FSGS or Non-recurrent FSGS. These findings, together with the data obtained from previous mouse studies in uPA null mice suggest that in contrast to cancer, uPA does not appear as crucial for suPAR mediated non-inflammatory glomerular injury such as FSGS.

suPAR Binds to and Activates β3 Integrin in Podocytes

In podocytes, uPAR binds to β3 integrin. In addition, suPAR is known to associate with β1 and β2 integrin. Thus, it was investigated if suPAR can bind to β3 integrin as well. Using co-immunoprecipitation of suPAR and β3 integrin, suPAR was found to interact with β3 integrin in a manner similar to the behavior of membrane-bound uPAR. GFP-E1F1B, which encodes a translation initiation factor, and Flag-Raver, which encodes a ribonucleoprotein PTB-binding 1, were used as negative binding controls.

Thus, we hypothesized that suPAR could activate β3 integrin, in a similar manner as membrane-bound uPAR in podocytes. The activity of β3 integrin is measured using the activation-epitope recognizing antibodies such as the anti-β3 integrin antibody AP5. Human differentiated podocytes were incubated with high-level suPAR containing recurrent FSGS sera (5%) in the absence or presence of a monoclonal uPAR blocking antibody and the peptide cycloRGDfV, which blocks β3 integrin activity. Recombinant human suPAR protein was used as a positive control, while bovine serum served as negative control. Twenty-four hours later, the expression and localization of AP5 signal, corresponding to activated β3 integrin, was analyzed by immunofluorescent staining. Human podocytes display low level activation of β3 integrin when grown in bovine serum or serum from healthy subjects. In contrast, incubation with sera from recurrent FSGS patients (i.e., suPAR-rich) or with recombinant suPAR strongly induces activation in a pattern (AP5 signal) highlighting areas of focal adhesions, which is known to be the location for β3 integrin. This activation could be blocked by specific inhibitors uPAR blocking antibody or cycloRGDfV.

β3 integrin activity in kidneys with glomerular disease was studied in a patient biopsy cohort (FIG. 2). AP5 staining is induced in glomeruli was found in seven of nine idiopathic FSGS patients, and in all recurrent FSGS patients. Moreover, a strong correlation was found between the extent of focal sclerosis and the number of AP5-positive glomeruli (r=0.65, P<0.01). In contrast, no or only weak AP5 signal was observed in glomeruli of healthy kidney or in MCD and MN, suggesting that induced podocyte β3 integrin activity is a specific feature of FSGS.

To prove that circulating suPAR affects the transplanted kidney by activating podocyte β3 integrin, the presence of AP5 signal was detected in podocytes by double immunofluorescent staining with synaptopodin, a podocyte marker, in post-transplant graft biopsies. β3 integrin activity was found to be low in graft podocytes before reperfusion, whereas it is remarkably increased two hours after reperfusion in recurrent FSGS (n=2), but not in non-recurrent FSGS (n=2). Moreover, the AP5 signal is higher on post-transplantation biopsies in recurrent FSGS (n=3) than in patients with non-recurrent grafts (n=5). As controls, AP5 signal is barely noticeable in normal kidney sections (n=2) and does not increase in kidney transplant biopsies in acute T-cell mediated rejections (n=3). Taken together, these findings suggest that increased podocyte β3 integrin activity is a feature of both native FSGS and FSGS recurrence.

Individual suPAR Serum Levels and Podocyte β3 Integrin Activity Determine Treatment Response of Plasmapheresis in Recurrent FSGS To further define the relationship between suPAR and podocyte β3 integrin activity, FACS analysis was performed for β3 integrin activity (using AP5 antibody) in cultured human podocytes incubated with sera from normal subjects, and with the pre-transplantation sera from non-recurrent FSGS and recurrent FSGS patients. To further study the effects of suPAR-containing patient sera on podocyte β3 integrin activity (AP5), differentiated human podocytes were incubated with pooled sera from normal subjects (n=5), pre-transplantation sera from non-recurrent FSGS (n=10), and recurrent FSGS patients (n=15). The cells were then assayed by FACS analysis for β3 integrin activity (AP5 staining as measured by mean fluorescence intensity, MFI). Recurrent FSGS pre-transplantation sera were found to have significantly elevated β3 integrin activity, as compared to non-recurrent FSGS and normal subject sera ($P<0.001$ for recurrent FSGS sera vs. non-recurrent FSGS sera or vs. normal subjects). In general, suPAR levels correlate well with the activity of podocyte β3 integrin visualized with A5 antibody.

It was then determined whether inhibiting suPAR could lower AP5 activity on podocytes. Co-incubation of recurrent FSGS pre-transplantation sera with anti-uPAR antibody or with cycloRGDfV results in a significant reduction of the FSGS sera induced podocyte β3 integrin activity. $P<0.01$ for cycloRGDfv co-treated cells vs. recurrent FSGS sera alone; $P<0.001$ for monoclonal anti-suPAR antibody co-treated cells vs. recurrent FSGS sera alone. Both direct blockade of suPAR and β3 integrin antagonist cycloRGDfv block the β3 integrin activation otherwise induced by the pre-transplantation serum from recurrent FSGS patients.

The current standard of care for recurrent FSGS is plasmapheresis, which usually consists of 1.5 liter (I) plasma volume that is pheresed before replacement with 5% albumin. To determine if suPAR could be removed by plasmapheresis, sera from recurrent FSGS patients (n=4) were collected right before and after a single course of plasmapheresis, then assayed for suPAR levels. Plasmapheresis could remove suPAR from the FSGS patient serum ($P<0.01$). Human podocytes were incubated with the sera from recurrent FSGS patients (n=6), which were collected before or after several plasmaphereses to determine their β3 integrin activity on podocytes. Podocyte β3 integrin activity caused by FSGS sera was significantly lowered by plasmapheresis ($P<0.001$ for podocyte AP5 activity with pre-pheresis sera vs. post-pheresis sera). To understand the effects of plasmapheresis on patient clinical outcome, four clinical cases of recurrent FSGS patients who received plasmapheresis after transplantation were studied. Patients (n=4) had elevated suPAR serum levels before transplantation. After serial plasmapheresis treatments, two patients reached a clinical remission with their serum suPAR levels falling below 2000 pg/ml. Importantly, their sera also lost the capacity to induce podocyte β3 integrin activity. Plasmapheresis reduced serum suPAR to a normal level and diminished β3 integrin activity to a normal range. In contrast, the other two patients remained in recurrence despite plasmapheresis. Their serum suPAR levels were still high and their sera still caused strong podocyte β3 integrin activity. Plasmapheresis failed to normalize the serum suPAR level and, more importantly, could not reduce β3 integrin activity to a value in the physiological range. These findings suggest that the disease stabilizing effects of plasmapheresis depend on lowering individual serum suPAR to levels that sharply modulate podocyte β3 integrin activity. Thus, an improvement was needed to remove suPAR from the circulation of patients refractory to treatment by plasmapheresis.

Since some FSGS patients who had similarly high levels of suPAR in their pre-transplantation sera did not develop recurrent FSGS and had low post-transplantation AP5 signal in graft podocytes, graft in integrin reactivity was examined. In a cohort of 333 end-stage kidney disease (ESKD) patients that were transplanted in the Canary Islands in Spain, 105 grafts were heterozygous and 11 grafts were homozygous for the $PIA_2$ polymorphism (Table 2). The $PIA_2$ polymorphism encodes for a β3 integrin that is susceptible to strong activation. Presumably, these patients are particularly sensitive when it comes to elevated suPAR blood levels and $PIA_2$ status might be considered as a second hit for suPAR-induced FSGS explaining why the few patients with similar suPAR levels (high or low) vary in how there FSGS disease varies before and after transplantation.

TABLE 2

β3 Integrin Polymorphisms $PIA_2$ Genotyping in Donors for ESKD

| Genotyping | Grafts in ESKD (n = 331) | Control (n = 100) |
| --- | --- | --- |
| LL | 212 (64.1%) | 66 (66.0%) |
| LP (heterozygous) | 108 (32.6%) | 32 (32.0%) |
| PP (homozygous) | 11 (3.3%) | 2 (2.0%) |

Injection of suPAR Causes Glomerular Deposition and Proteinuria

To determine if suPAR is a cause or consequence of FSGS, three different murine models of kidney disease were established: (1) injection of recombinant suPAR into uPAR knockout ($Plaur^{-/-}$) mice, (2) endogenous suPAR release model in a hybrid-transplant mice, and (3) genetically engineered mice overexpressing suPAR in the blood.

First, it was determined whether exogenous circulating suPAR could deposit into kidneys and cause albuminuria. $Plaur^{-/-}$ mice were injected with escalating dosages of recombinant mouse suPAR intravenously. Low dose injection at 2 μg and 10 μg did not cause albuminuria, which is consistent with a physiological (low) concentration of suPAR in the blood of healthy subjects (n=4 in each group). But dosages of 20 μg and above lead to induction of transient albuminuria within 24 hours (n=4 in each group) that resolved within 2-3 days. $P<0.01$ for mice injected with 20 μg suPAR at 24 h vs. mice injected with other doses, or vs. other time points. suPAR injected $Plaur^{-/-}$ mice were sacrificed and their kidneys were removed for immunostaining. Prominent deposition of suPAR was observed within close vicinity of podocytes in $Plaur^{-/-}$ mice that had received 20 μg of suPAR, but not in $Plaur^{-/-}$ mice that received only 2 μg. Moreover, this deposition was associated with an increase in β3 integrin activity on podocytes as exhibited by increased AP5 labeling that again was suPAR dose dependent.

suPAR Causes Podocyte Disease in $Plaur^{-/-}$ Donor Kidneys

Second, it was determined whether an increased level of endogenous suPAR causes kidney disease in wild-type mice. LPS has been shown to increase suPAR in the blood of human subjects through release from monocytes. Thus, it was determined whether LPS could also enhance suPAR blood levels in mice. Indeed, LPS injection caused a strong increase of suPAR in sera and urine of mice (n=6) up to five-fold over the levels observed in control mice (n=6). Serum suPAR levels increase significantly 24 h, decrease 48 h after LPS injection, but are still significantly higher compared to controls. $P<0.001$ for LPS injected mice at 24 h vs. PBS control, and vs. at 0 h. $P<0.01$ for LPS injected mice at 48 h vs. at 0 h. In urine, the levels of suPAR induced by LPS were higher and peaked 48 h after LPS. $P<0.001$ for LPS injected mice at 48 h vs. 0 h, and vs. PBS control at any point. $P<0.01$ for LPS mice at 24 h vs. 0 h. Kidney hybrid mice were generated in which one kidney from wild-type mice was removed and then a $Plaur^{-/-}$ kidney was engrafted. These hybrid mice fully recovered within 14 days after surgery and had normal renal function and structure. Five hybrid mice were then injected with a single low dose of LPS to stimulate suPAR; three hybrid mice were injected with PBS as a negative control. Twenty-four hours later, the kidneys were removed for EM analysis. Normal filtration barriers were present in both graft and native kidneys in negative-control hybrid mice. Immunohistochemistry of uPAR shows low level of uPAR expression in glomeruli of the native wild-type kidney, but none in the transplanted $Plaur^{-/-}$ kidney. In contrast, the LPS-injected hybrid mice show significant foot process effacement both in the native wild-type kidney as well as in the engrafted $Plaur^{-/-}$ kidney. PBS-injected hybrid mice show low levels of uPAR expression in glomeruli of the native wild-type kidney and none in the transplanted $Plaur^{-/-}$ kidney. With the LPS-injected mice, however, immunohistochemistry indicates strong uPAR expression in the glomeruli of native wild-type kidney. Interestingly, a strong suPAR signal is also observed in the transplanted $Plaur^{-/-}$ kidney, indicating endogenously induced suPAR deposits in the kidney. There was also prominent podocyte foot process effacement in $Plaur^{-/-}$ as well as in the wild-type kidney. Since $Plaur^{-/-}$ mice are generally protected from LPS induced proteinuria and podocyte effacement, the podocyte effacement of the $Plaur^{-/-}$ graft is best explained by deposited suPAR that stems from the wild-type host leading to excessive podocyte β3 integrin activation in the graft.

Prolonged Elevation of Circulating suPAR Causes FSGS-Like Glomerulopathy

Third, to explore if prolonged elevation of suPAR in the sera of mice causes a progressive glomerulopathy, wild-type mice were engineered that drive expression of suPAR from skin. A mouse suPAR plasmid was made based on a known coding sequence for secreted suPAR, which contains DI and DII domains. As a control, a β3 integrin binding deficient suPAR mutant was generated. This mutant has a point mutation on domain DII and was termed E134A. Plasmids were delivered into mice skin by in vivo electroporation into skin. Both forms of mouse suPAR express equally well following electroporation. GFP-EIF1B is used as a negative binding control. Expression of protein is confirmed by separate immunoblotting for Flag-tagged protein or for GFP tagged protein. To investigate if suPAR could induce a progressive glomerular disease, in vivo gene delivery of suPAR was used to enhance suPAR expression in the sera of electroporated mice. suPAR levels in sera and urine start to rise two days after electroporation, which was repeated once a week for a sustained elevation of blood suPAR levels over the course of the analyzed time period. The serum level of suPAR peaks after one week. $P<0.05$ at day 7 vs. day 0 (before initial electroporation). Comparatively, more suPAR is observed in urine. $P<0.001$ for day 7, 14 and 28 vs. day 0; $P<0.05$ for day 28 vs. day 7. No difference of blood or urine suPAR level is observed for wild-type suPAR or the suPAR mutant E134A, which serves as a control (n=4 in each group).

Urine was collected daily before and after suPAR gene delivery for albumin and creatinine measurement. Coinciding with the rise of suPAR in the sera of mice, albuminuria was induced and it persisted over the course of the four week investigation. Urine albumin significantly increases at day 7 after initial suPAR electroporation, and it peaks at day 14 in mice that express wild-type suPAR. In contrast, no significant albuminuria is observed in mice that express E134A, suggesting that binding of suPAR to β3 integrin is an important characteristic of suPAR-induced renal injury. $P<0.05$ for suPAR engineered mice at day 7 vs. before treatment. $P<0.01$ for suPAR engineered mice at day 14 vs. before treatment, or vs. E134A treated mice at day 7 or day 14.

Five glomeruli are randomly picked from each mouse and the extent of foot process effacement is assessed semi-quantitatively by relating the length of glomerular basement membrane covered by effaced processes to the total length of the glomerular basement membrane. While severe and extended foot process effacement is found after four weeks in mice engineered with wild-type suPAR, no significant effacement is found in mice engineered with mutant E134A. Thus, prominent foot process effacement consistent with glomerular disease was noted in the ultrastructure of podocytes only in mice that express suPAR capable of binding β3 integrin. To study if the suPAR-induced glomerulopathy behaves more like MCD or FSGS, the kidneys were analyzed by light microscopy and histochemistry. The abnormalities in kidney morphology are observed as early as two weeks after initial suPAR gene overexpression and aggravated by four weeks. H&E and PAS staining revealed features of a progressive glomerulopathy, including hypercellularity, mesangial expansion, mesangiolysis and occasional tuft adhesions were found. Of note, immune complex deposition was not detected in any of the mice analyzed. Semi-quantitative histopathological scoring revealed indices of a progressive glomerulopathy reminiscent of early FSGS. Importantly, these changes were absent in mice that express the E134A suPAR mutant incapable of β3 integrin binding (FIG. 3).

To further study the disease-causing effect of suPAR, its action was blocked. A monoclonal anti-uPAR antibody was administered to mice engineered to express high serum suPAR levels. They were treated with uPAR blocking antibody every two days up to four weeks, control mice received the same amount of isotype IgG (n=4 for each group). Urine was collected every day from both groups, and assayed for total protein and creatinine. While increased proteinuria was found in mice with high serum suPAR that received IgG isotype control, administration of the anti-uPAR antibody protected the mice from high serum suPAR induced renal disease. $P<0.05$ for suPAR mice given isotype control at day 7 vs. before initial electroporation day 0, or vs. mice treated with anti-uPAR antibody at day 7; $P<0.01$ for suPAR mice given isotype control at day 21 vs. at day 0, or vs. anti-uPAR antibody treated mice at day 21. Morphological examination of kidneys in mice that received four weeks of anti-uPAR treatment indicates improved histopathology scores as compared to those animals that received isotype control antibody (FIG. 4). As indicated by H&E and PAS staining, there is no overt renal injury with the suPAR engineered mice that received anti-uPAR antibody. In contrast, the mice that received control antibody show significant kidney damages reminiscent of FSGS at an early phase, similar to that observed with the wild-type suPAR engineered mice. Semi-quantitative EM analysis shows significantly improved podocyte foot process structures in the anti-uPAR antibody treatment group (i.e., only focal effacement), in contrast to suPAR overexpressed mice that received control antibody and developed severe foot process effacement. P<0.01 for IgG isotype control vs. anti-uPAR antibody treated mice in the ratio of effaced foot process against total GBM length measured. Taken together, this data suggests that neutralization of suPAR action can improve suPAR-induced renal injury.

Discussion

The present study demonstrates that suPAR is a circulating serum factor that can cause FSGS. This conclusion is based on the human studies that show elevated serum levels of suPAR in a population of pediatric and adult FSGS patients and on animal models with engineered suPAR overexpression that develop a renal disease characteristic of FSGS. High pre-transplantation serum suPAR levels are associated with the presence of native FSGS and also constitute a significantly increased risk for recurrent FSGS after transplantation. One year after kidney transplantation, suPAR levels remain significantly elevated in patients that develop FSGS recurrence. The mechanism of injury caused by FSGS associated suPAR is through activation of β3 integrin on podocytes, an event sufficient to initiate podocyte foot process effacement and proteinuria. The level of podocyte β3 integrin activity that is driven by suPAR depends on the amount of individual serum suPAR and possibly also on suPAR post-translational modification (i.e., glycosylation status), and appears to be independent of total serum uPA levels, which is in contrast to suPAR-uPA associations in some forms of cancer. Thus, interference in pathogenesis by removing suPAR from the circulation can protect a subject from suPAR-mediated podocyte injury. The level of suPAR must be reduced to a level (measured as an absolute amount, concentration in the circulation, or relative amount as compared to another serum protein) sufficient to stop or slow disease pathogenesis by reducing podocyte β3 integrin activity.

Since the first clinical description of nephrotic syndrome recurrence after kidney transplantation, there has been mounting evidence suggesting the presence of a circulating permeability/FSGS factor, both for native and transplant FSGS. Savin and colleagues proposed the existence of a glycol-protein from 30 to 50 kDa in FSGS patients, which could be removed by plasmapheresis. But the molecular identity and the mechanisms of action have hitherto not been elucidated. Based on our showing that podocyte-produced membrane-bound uPAR is induced in FSGS to pathologically activate β3 integrin, thereby causing foot process effacement and proteinuria, a candidate approach was taken and the role of circulating suPAR in FSGS was examined. After observing high levels of serum suPAR in pre- and post-transplant FSGS, murine models were created that could explore the cause or effect nature of suPAR. Interestingly, different forms of suPAR were found that correspond to different domain fragments in the sera of FSGS patients, having molecular weights ranging from 22 kDa to 45 kDa. This is close to the molecular range (from 30 kDa to 50 kDa) of the FSGS permeability factor predicted from the work of Savin et al.

The present study provides a measurable predictor of FSGS risk in patients with FSGS before and after transplantation. As it stands, approximately 75% of patients with FSGS have elevated levels of suPAR compared to other glomerular diseases such as MN, MCD and pre-eclampsia. This accords with the known pathology involving phospholipase A2 receptor antibodies in MN and angiopoietin-like 4 or c-mip in MCD. Since suPAR is detectable both in healthy human subjects and normal mice, physiological suPAR levels or physiological suPAR domain combinations do not appear to be harmful. But there may be other factors in FSGS patients that make them susceptible to disease or its recurrence. Another interesting question is why a few FSGS patients without elevated suPAR levels still develop FSGS as well as recurrent FSGS? An obvious answer would be that suPAR can act in concert with podocyte uPAR and this might drive FSGS even in the absence of higher suPAR levels. Thus, reducing the level of suPAR in the circulation of a subject below physiological levels may be warranted.

Methods

Patients

Sera were collected from 78 patients with FSGS, 25 patients with Minimal Change Disease (MCD), seven patients with pre-eclampsia, 16 patients with membranous nephropathy (MN), and 22 normal subjects. Note that two pairs of identical twins were included. In each case, while one was unaffected, his twin brother had FSGS. These patients were enrolled in seven different medical centers. The study was approved by the institutional review board of each participating center. For transplant FSGS patients, the age at transplantation was 28.1±15.7 years old for non-recurrent FSGS, 26.6±15.7 years old for recurrent FSGS. The male versus female ratio was 16:8 for non-recurrent FSGS and 15:15 for recurrent FSGS. All transplant patients received immunosuppressive induction and maintenance, as well as pre- and post-transplantation care (*Renal Transplant Protocols*, Royal Infirmary of Edinburgh, 4th Edition, 2007). Recurrence was defined as spot urine protein-to-creatinine ratio>3.5 g/g during the first 30 days after transplantation. For those patients with native kidney proteinuria at the time of transplantation, a stent was placed in the transplanted kidney to measure transplant proteinuria and then removed in the outpatient clinic 2-3 weeks later.

ITGB3 Genotyping for $PIA_2$

Genotyping for β3 integrin polymorphism $PIA_2$ (Leu33Pro) was performed in donors for kidney transplantation patients as reported previously (Salido et al., 3. Am. Soc. Nephrol. 10:2599-2605, 1999).

Murine Models

Injection of Recombinant suPAR into $Plaur^{-/-}$ Mice

To determine whether circulating suPAR could deposit into the kidney and affect the renal ultrafiltration function, escalating doses were injected i.v.: 2 μg, 10 μg or 20 μg of recombinant mouse suPAR(R&D Systems) into $Plaur^{-/-}$ mice (female, 20±2.0 g) through the tail vein. $Plaur^{-/-}$ mice were originally on a mixed background of 75% C57BL/6 and 25% 129, but back-crossed to C57BL/6 mice for ten generations before any use. Urine was collected before injection and every 12 hours after injection for albumin and creatinine analysis. Twenty-four hours after injection, the $Plaur^{-/-}$ mice were sacrificed and the kidneys were snap-frozen for immunofluorescence.

Hybrid Mouse, Transplantation, and LPS-Mediated suPAR Release

To determine whether the endogenously induced suPAR could cause podocyte injury, a hybrid mouse model was established through cross-kidney transplantation. (n=10). The right side kidney was harvested en bloc from $Plaur^{-/-}$ mice. This $Plaur^{-/-}$ kidney was designated as the donor kidney, while wild-type mice with the native right kidney removed were the recipients. They had a baseline level of uPAR in the glomerulus and a low level of suPAR in the blood. Transplantation surgery was performed following a previously published protocol with slight modification (Coffman et al., J. Immunol. 151:425-435, 1993; Han et al., Microsurgery 19:272-274, 1999). In brief, under anesthesia, the right side kidney, ureter were harvested en bloc, including the renal artery with a small aortic cuff and the renal vein with a small caval cuff from the Plaur$^{-/-}$ mice (female, 20±2.0 g) (Han et al., 1999). Grafts were perfused in situ with 0.5 ml cold Ringer's lactate containing 10 U/ml heparin.

Anastomosis was made between the vascular cuffs and the recipient's abdominal aorta and inferior vena cava using end-to-side suture technique. Finally, for the anastomosis of the ureter, the recipient bladder was pierced though with a 21 g needle, the ureter was pulled through, and the periuretal tissue was stitched to the exterior wall of the bladder. Kidney graft survival was followed by daily examinations of overall animal health and grafts were monitored by the measurement of blood serum creatinine and urea nitrogen. Fourteen days after surgery, no rejection was observed in any of the transplanted mice.

Fourteen days after surgery, two animals were sacrificed for light and electron microscopy to analyze structural integrity of native and transplanted kidneys. Five hybrid mice were treated with lipopolysaccharide (LPS) (Sigma) at 10 mg/kg body weight, i.p. to induce suPAR levels in the blood, while three hybrid mice received the same amount of PBS as controls. Twenty-four hours after LPS treatment, both the native and transplant kidneys were removed for electron microscope and immunostaining for suPAR.

Site-Directed Mutagenesis

Site directed mutagenesis was performed with QuikChange® II XL Site-Directed Mutagenesis Kits (Stratagene) following the manufacturer's protocol. The plasmid carrying mouse suPAR cDNA (GenBank Accession No. BC010309) was used as a template. Different primer pairs aimed at mutating the suPAR sequence in DII were generated. Following the site mutagenesis, the newly created uPAR mutants were co-transfected into the HEK cells with mouse β3 integrin plasmid respectively. Co-immunoprecipitation was then performed to look at the binding ability of different suPAR mutants with β3 integrin. The suPAR mutant that was found deficient in binding fβ3 integrin (i.e., E134A) was then chosen for further use.

In Vivo Gene Delivery and Electroporation

To investigate whether sustained elevation of suPAR could cause a progressive glomerular disease and FSGS, plasmids encoding mouse suPAR were expressed in wild-type mice. Under anesthesia, a plasmid encoding suPAR (domains DI-DII) (40 µg in PBS) was injected intradermally into and bilaterally in the hind legs, followed by in vivo electroporation with the Derma Vax™ DNA delivery system (Cyto Pulse Sciences). For control, a mutant mouse was generated with suPAR plasmid, E134A, which was deficient in binding in integrin, as described above. Gene delivery was done once a week up to six weeks. Blood and urine were collected before and after each gene delivery for analysis. Each week four mice were sacrificed for examination of kidneys.

Blocking Studies

To further confirm the effect of suPAR, four mice undergoing suPAR in vivo gene delivery were randomly chosen to receive monoclonal anti-mouse uPAR antibody (R&D Systems, 500 µg/kg), while the other four mice received the same amount of isotype IgG control. First, anti-uPAR antibody was administered one day after the initial suPAR gene delivery, followed by once every three days up to four weeks. Urine was collected daily, and the kidney was harvested for examination four weeks after initial gene delivery.

Serum suPAR and uPA Measurement

The concentration of circulating suPAR in human subjects was quantitated by Quantikine Human uPAR Immunoassay kit (R&D Systems) following the manufacturer's protocol. Mouse suPAR was evaluated by an in-house enzyme linked immunosorbent assay (ELISA) (Tjwa et al., J. Clin. Invest. 119:1008-1018, 2009). The concentration of serum uPA was measured by IMUNBIND uPA ELISA kit (American Diagnostic).

Flow Cytometry

To quantitate the activity of 83 integrin on human podocytes, flow cytometry was performed on a FACScan instrument and analyzed with Cellquest software (Becton Dickinson). Briefly, the fully differentiated human podocytes were treated with human sera (5%) or suPAR recombinant protein for 24 h. Cells were thereafter scrapped off the culture plates and resuspended. AP5 antibody (1:50) was added and incubated for 30 m at room temperature (RT). After sufficient wash with the flow buffer, the cells were further incubated with secondary antibody Alexa Fluor® 488 goat anti-mouse IgG (Invitrogen, 1:500) for 20 m. The cells were fixed with 2% paraformaldehyde (PFA) and analyzed using FACScan (Becton Dickinson). Cells incubated with isotype IgG1 were used as a negative staining control.

Cell Culture and Transfection

Conditionally immortalized human podocytes were cultured as described previously (Saleem et al., J. Am. Soc. Nephrol. 13:630-638, 2002). In brief, podocytes were proliferated and maintained at 33° C. in RPMI-1640 medium (Invitrogen), containing 10% FBS and 1% insulin transferrin-selenium (Sigma). Cultured podocytes were seeded on coverslips and allowed for differentiation for 14 days at the growth-restrictive temperature of 37° C. before any treatment. To study the effect of different sera on podocytes, conventional podocyte medium was removed and changed into RPMI-1640 medium containing 4% human sera. Recombinant human suPAR protein (R&D Systems) was used at 1 mg/ml. To investigate sera induced cellular effects due to the activation of uPAR-β3 integrin pathway, monoclonal anti-uPAR antibody (R&D Systems, 1 mg/ml) and cycloRGDfV (Biomol, 1 mg/ml), a αvβ3 integrin inhibitor was co-incubated with recurrent FSGS sera respectively. Twenty-four hours after treatment, human podocytes were fixed with 4% PFA before immunofluorescence labeling. To study the interaction of suPAR and β3 integrin, human embryonic kidney (HEK) 293 cells were cultured in DEME medium containing 10% FBS at 37° C. Upon 90% of confluency, cells were co-transfected with GFP— or Flag-tagged mouse membrane-bound uPAR (Genbank Accession No. NM_011113) or suPAR (Genbank Accession No. BC010309) plasmids along with plasmids carrying mouse β3 integrin (Genbank Accession No. NM_016780), GFP-E1F1B, which encodes a translation initiation factor, and Flag-Raver, which encodes a ribonucleoprotein. PTB-binding 1 was also co-transfected to serve as negative binding control for subsequent co-immunoprecipitation studies. Transfection was performed with Lipofectamine™ 2000 (Invitrogen), following the manufacturer's instruction. Twenty-four hours after transfection, HEK cells were harvested for further use.

Immunohistochemistry and Immunofluorescence

To analyze the activity of β3 integrin on cultured human podocytes, the coverslip with fixed podocytes was incubated with a blocking buffer (5% goat serum, 5% donkey serum) (see Cell Culture section for details) for 30 m at RT, then with AP5 antibody (GTI, 1:50) for 1 h. After washing three times with PBS for 3 m each, the secondary antibody, Alexa Fluor® 488 Goat Anti-Mouse IgG (Invitrogen, 1:1000) was added and incubated for 45 m. The coverslip was then washed with PBS and counter stained for peroxidase activity with 4',6-diamidino-2-phenylindole (DAPI, 3 mM, Invitrogen) for 5 m. The sections were dehydrated and mounted in Bio Mount (Bio Optica). Specificity of antibody labeling was demonstrated by the lack of staining after substituting PBS and proper control immunoglobulins (Invitrogen) for the primary antibody.

To investigate expression of uPAR and β3 integrin activity in mouse glomeruli, cyrosections were cut from the OCT embedded kidney tissue blocks and fixed in cold acetone for 10 m. The section was incubated with blocking buffer for 30 m, then with mouse (1:1, for double immunostaining with uPAR) or rabbit (1:100, for double immunostaining with AP5) anti-synaptopodin antibodies (gifts from Dr. Peter Mundel, University of Miami) for 1 h. After washing with PBS, the section was further incubated with either the goat anti-mouse uPAR antibody (R&D Systems, 1:50) or AP5 antibody (1:50) for 1 h, followed by the secondary antibody duos (Alexa Fluor® 488 and Alexa Fluor® 546, Invitrogen) matched to the two primary antibodies for 45 m. Finally, the section was washed serially with PBS and $H_2O$ before mounted for imaging. Images were acquired by a Leica TCS SP5 Confocal Microscope or a Leica DMI6000B fluorescence microscope.

To examine the activity of glomerular β3 integrin in humans, double immunofluorescent staining was performed on podocytes. Kidney tissue was obtained from renal biopsies of primary FSGS (n=9), recurrent FSGS after transplantation (n=6), MCD (n=5) and MN (n=5). The healthy pole of three nephrectomized kidneys with tumors was used as control. Samples were fixed in 4% PFA and embedded in paraffin. Sections were cut, deparaffinized, and rehydrated, then treated with microwave irradiation in 10 mM citrate buffer (pH 6.0) to retrieve antigens Thereafter, the sections were incubated with 0.5% avidin (Sigma) and 0.01% biotin (Sigma) to suppress endogenous avidin-binding activity, and with 3% hydrogen peroxide to block endogenous peroxidase. Then the sections were sequentially incubated with the primary antibody AP5 (GTI, 1:50) for 1 h, the secondary biotinylated goat anti-mouse IgG (Invitrogen), and with the peroxidase-labeled streptavidin (Invitrogen).

Immunoprecipitation and Western Blot

Co-immunoprecipitation was performed to examine the interaction between suPAR and β3 integrin following our published protocols (Wei et al., Nature Med. 14:55-63, 2008). Briefly, 24 hours after transfection with desired GFP- or Flag-tagged plasmids, HEK cells were lysed in RIPA buffer (Boston Bioproducts) containing protease inhibitor cocktail (Roche) for 30 m on ice. After centrifugation at 14,000 rpm for 20 m, the supernatant (i.e., the lysate) was collected and its total protein concentration measured. The lysates which carried about 500 mg total protein were then incubated with the Flag beads, anti-Flag M2 affinity gel (Sigma) overnight at 4° C. to pull down the Flag fusion protein and its interactome. After washing five times with RIPA lysis buffer for 10 m each, the Flag beads were harvested via centrifuge, resuspended in the NuPAGE LDS sample buffer (Invitrogen) and incubated at 70° C. for 10 m. After brief centrifuge, the eluates (the supernatant that contains the Flag fusion protein and its interactome) were then collected for Western blotting.

For Western blotting, the eluates as well as the HEK lysates that served as co-immunoprecipitation input controls, were loaded into the NuPAGE 4-12% Bis-Tris Gel (Invitrogen) for electrophoresis. After separation, proteins were transferred to the PVDF membrane. The membrane was then incubated with the primary anti-Flag (Sigma, 1:1000) or anti-GFP (Abcam, 1:1000) antibodies after blocking with 5% milk for 1 h at RT or overnight at 4° C. After sufficient wash in the Tris-buffered saline/0.2% Tween-20 (TBST) buffer, the membrane was then incubated with goat anti-mouse (1:10,000 for Flag) or goat anti-rabbit (1:10,000 for GFP) secondary antibody (Promega). Finally, the blots were incubated with SuperSignal West Pico Chemiluminescent Substrate (Thermo Scientific) for 5 m and exposed to Kodak autoradiography film (Kodak). The film was then developed using a Kodak X-OMAT 2000A processor (Kodak).

Immunoprecipitation was used to determine the presence of suPAR in human sera. For each reaction, 30 ml of human serum either from the healthy subjects or recurrent FSGS patients was diluted with the phosphate buffer saline (PBS) into total volume of 500 ml and incubated with 20 ml Protein A/G PLUS agarose beads (Santa Cruz Biotechnology) for 1 h at 4° C. After centrifuge, the beads were removed and 3 mg of mouse anti-human uPAR(R&D Systems) antibody as well as 20 ml protein A/G PLUS agarose beads were added to the supernatant. The mixture was incubated overnight at 4° C. before washing five times with PBS for 10 m each. Then the supernatant, hereinafter called uPAR pulldown, was resuspended in LDS sample buffer and eluated from the Protein A/G PLUS agarose beads. To detect the presence of suPAR in recurrent FSGS patient sera, the uPAR pull-down was loaded onto a NuPAGE 4-12% Bis-Tris gel, transferred to PVDF membrane and then blotted with a rabbit polyclonal anti-human uPAR antibody (Santa Cruz, 1:200). In order to know whether the serum suPAR is in free form or bound with albumin, the uPAR pull-down was loaded onto the NuPAGE 4-12% Bis-Tris Gel, and was blotted against a mouse anti-human albumin antibody (Abcam, 1:1000). One ml of human sera was loaded as the positive control for human albumin. For reverse immunoprecipitation, human sera was pulled down by the above anti-human albumin antibody, and the precipitates was immunoblotted with rabbit anti-human uPAR antibody (Santa Cruz, 1:200) or rabbit anti-human adiponectin antibody (Abcam, 1:1000) respectively.

Transmission Electron Microscopy, Light Microscopy, and Histochemistry

TEM was done as described by Wei et al. (2008). Mouse kidney tissues were examined and scored by a nephropathologist in a blinded fashion according to a previously-described scoring system (Crowley et al., J. Clin. Invest. 119:943-953, 2009). In brief, fixed kidney tissues were embedded in paraffin, sectioned, and stained with hematoxylin and eosin (H&E) and Periodic Acid Schiff (PAS). The kidney sections were graded based on presence and severity of abnormalities in glomeruli, tubules, vessels, and interstitium. The severity of renal pathological abnormalities was graded using a semi-quantitative scale, in which 0 represented no abnormalities, and 1+, 2+, 3+, and 4+ represented mild, moderate, moderately severe, and severe abnormalities, respectively. A histological score for each kidney was obtained by summing the individual grades for the glomeruli, tubules, and interstitium plus one point for the presence of vascular damage or arterial stenosis. Percentage glomerulosclerosis is defined as the number of glomeruli with evidence of sclerosis divided by the total number of glomeruli in the section.

Statistical Analysis

Statistical analyses were performed by one-way ANOVA or Student's paired or non-paired t-test. The null hypothesis was rejected at P value 0.05. Values are presented as mean±S.D. unless otherwise stated.

Example 2

In this study, the implications of serum suPAR were evaluated on the etiology of primary FSGS, response to therapy, and disease progression. Circulating suPAR was analyzed in two distinct, medically-treated, biopsy-proven, primary FSGS cohorts containing children and adults. Seventy patients were from the North American-based randomized FSGS clinical trial (FSGS-CT) and 94 patients were from the European-based consortium for study of steroid resistant nephrotic syndrome (PodoNet).

Circulating suPAR levels were found to be markedly elevated in the majority of FSGS patients in both FSGS-CT (84.3%) and PodoNet (55.8%) cohorts, compared to control subjects (5.4%) (P<0.0001). In the FSGS-CT subgroups, serum suPAR levels increased minimally in cyclosporine-treated patients, but decreased significantly in mycophenolate mofetil (MMF)-treated patients (5064 pg/ml±292 pg/ml vs. 4113 pg/ml±264 pg/ml, P<0.01). Moreover, a decline in serum suPAR levels over the course of 26 weeks of treatment was associated with achieving a stable complete remission. In the PodoNet cohort, familial or genetic FSGS patients due to a NPHS2 mutation had higher suPAR levels than non-genetic cases.

This study shows that suPAR levels are elevated in geographically and ethnically diverse patients and across patients with genetic/familial and non-familial types of FSGS. The change in circulating suPAR over time induced by different therapeutic regimens and the correlation with remission status supports the role of suPAR in the pathogenesis of FSGS.

Elevated Circulating suPAR Levels in Distinct FSGS Cohorts

Circulating suPAR was measured in 110 control subjects, 70 primary FSGS patients from the FSGS-CT cohort, and 94 primary FSGS patients from the PodoNet cohort (FIG. 5). Control subjects were age matched for PodoNet FSGS patients. There was no significant difference in sex distribution in the groups. Compared to control subjects, the serum suPAR levels in FSGS patients were markedly increased in both FSGS cohorts (P<0.001 for FSGS-CT vs. control, PodoNet vs. control, FSGS-CT vs. PodoNet). Using a cutoff value of 3000 pg/ml to define an abnormal concentration, the baseline circulating suPAR level was elevated in 84% of FSGS patients in FSGS-CT compared to 56% of FSGS patients in PodoNet. The mean suPAR level was higher in the FSGS-CT cohort than in the PodoNet cohort (4588 pg/ml±203 pg/ml vs. 3497 pg/ml±195 pg/ml, P<0.0001).

Characteristics of FSGS-CT Patients

Circulating suPAR levels, measured from sera collected at baseline (W01) and after 26 weeks (W26) of treatment, were analyzed for correlation with demographic variables and serum creatinine, serum albumin, estimated glomerular filtration rate (eGFR), or proteinuria (Up/c). While no analyzed variable was found predictive for the suPAR level at W01, serum albumin at both baseline and 26 weeks, and Up/c at 26 weeks were correlated with suPAR level at 26 weeks (FIG. 6).

To explore the effect of treatment on suPAR levels in the circulation, samples were analyzed in patients who were randomly assigned to either the CSA or MMF/dexamethasone arm of the trial. At baseline, there was no difference between the two treatment arms in age at sampling, age at disease onset, gender, race, proteinuria, serum albumin, serum creatinine, or eGFR (FIG. 7) as well as circulating suPAR levels by univariate analysis. After 26 weeks, however, suPAR level was significantly higher in the CSA arm than that in the MMF arm of the study (P<0.01). When examining the alteration from baseline to 26 weeks, suPAR level was increased in CSA arm, but decreased in MMF arm and the changes in suPAR levels between the two arms were significant (P<0.05). In line with the alteration of suPAR from baseline to 26 weeks between the two groups, there was also a significantly greater decrease in Up/c (P<0.05) and serum creatinine (P<0.001) in patients assigned to MMF arm compared to the CSA arm.

The clinical outcome for FSGS-CT patients was considered favorable if they achieved complete remission at week 26. Of the 70 patients in the FSGS-CT cohort with samples available for suPAR analysis, nine achieved complete remission at week 26 regardless of treatment. Although there was no significant overall change in suPAR levels, suPAR was clearly increased from baseline to week 26 in those four patients whose proteinuria recurred at week 52, while suPAR level was decreased in those five patients who achieved stable remission for at least six months. The same trend was observed in patients who achieved complete remission at week 52.

To further explore the alternations in circulating suPAR levels in response to therapy, patients were stratified into responders whose serum suPAR was elevated at baseline but dropped to below 3000 pg/ml after 26 weeks of treatment, and nonresponders whose suPAR remained high (at or above 3000 pg/ml) after 26 weeks of treatment. In total, there were nine responders: six from the MMF arm and three from the CSA arm. There was no difference of Up/c between responders and nonresponders at baseline. But Up/c was decreased dramatically all the way from the start (6.43±1.84) to the end of treatment (0.33±0.15, P<0.001 vs. baseline) and stabilized up to 78 weeks (0.61±0.25, P<0.001 vs. baseline) for suPAR responders, while it was decreased by less than 40% for suPAR nonresponders (4.95±0.49 at baseline vs. 3.06±0.62 at the end of the treatment, P<0.001).

In the FSGS CT cohort, none of the patients analyzed for suPAR levels had a disease causing genetic mutation in NPHS2, INF2, or PLCE1.

Characteristics of PodoNet FSGS Patients

In the PodoNet cohort, multi-regression analysis showed circulating suPAR levels were correlated with serum creatinine (P<0.01) and eGFR (P<0.05), but not with proteinuria, or with age at disease onset, age at sampling, or with sex in the PodoNet cohort. As there were a substantial number of familial cases or FSGS patients with a defined genetic mutation (NPHS2), this cohort was further stratified into two subgroups, familial/genetic versus non-genetic FSGS (FIG. 8). There was no difference with regard to age at disease onset, age at sampling, sex breakdown, eGFR, or serum albumin and creatinine level between the two subgroups. Proteinuria however was higher in the familial/genetic subgroup. Interestingly, the circulating suPAR level was significantly higher in familial or genetic FGSS group, when compared to levels in the non-genetic cases of primary FSGS (P<0.05).

In contrast to FSGS-CT, where patients were randomly assigned to either CSA or MMF therapy, treatment in PodoNet was at the discretion of the attending physicians. For the purpose of this analysis, patients were grouped according to the medication they received at the time of blood sampling: MMF or a calcineurin inhibitor. FIG. 9 analyzes the characteristics of patients who received MMF and those who did not. Overall, there was no significant difference between the two groups based on their demographic features or laboratory measurements (e.g., proteinuria, serum albumin, eGFR, and serum creatinine). Circulating suPAR levels were, however, significantly lower in the MMF-treated group (P<0.05). The same pattern was observed in patients who received MMF and prednisone, compared to those received other medications. In contrast, no difference of suPAR level was observed between patients who received CSA and those who did not have CSA. Finally, the circulating suPAR level was significantly lower in patients received MMF and prednisone, compared to that in patients who received CSA and prednisone (P<0.05).

Discussion

Elevated suPAR levels are found in primary FSGS. suPAR could enter the glomerulus, and bind to and activate β3 integrin on the podocyte sole plate to cause foot process effacement and proteinuria. We concluded the following: (1) the circulating suPAR levels were markedly elevated in the majority of patients with primary FSGS in two distinct cohorts; (2) MMF therapy was associated with a decrease in serum suPAR over time; (3) a decline in suPAR levels over the course of 26 weeks of treatment in the FSGS-CT was associated with a clinically stable complete remission; and (4) in patients with primary FSGS, suPAR levels were significantly higher in familial cases or those with a defined podocin mutation.

A key strength of this study is the determination of plasma suPAR levels in a large heterogeneous sample of patients with wide ranging ethnicity and racial backgrounds. The patients were well characterized phenol-typically with information about response to treatment and kidney function. Moreover, the PodoNet cohort includes a sizable subset of patients with a genetic cause of FSGS. The consistently high levels of suPAR in the circulation underscore the potential role of this molecule in the pathogenesis of all forms of primary FSGS.

Using a cut-off value of ≥3000 pg/ml, the suPAR level was elevated in 56-84% of patients with FSGS in these two distinct cohorts. Thus, a high level of serum suPAR is a characteristic feature in the majority of cases of FSGS. The differences in mean suPAR level and the number of patients with an abnormally high concentration between the FSGS-CT and PodoNet cohorts may reflect the younger age of the European group and racial and ethnic differences. Female children in the PodoNet cohort had higher suPAR levels than male patients. Gender differences have also been documented in another study that detailed elevated suPAR levels. This phenomenon, which was not observed in the American FSGS-CT patients, warrants further study. Similar to the findings from our previous report comprised of a mixture of heterogeneous primary FSGS patients containing those on medical therapy and those who received a kidney transplant, this study shows that elevated serum suPAR levels correlate with the presence but not with the amount of proteinuria. In the FSGS-CT cohort, the circulating suPAR levels at baseline were not correlated any analyzed variables. In contrast, suPAR at 26 weeks were correlated with serum albumin and Upc at 26 weeks. This suggests that changes in circulating suPAR level in response to treatment may reflect the underlying cause of the FSGS disease course and process. This is reinforced by the observation that a distinct decline of suPAR level to <3000 pg/ml within the first six months of treatment was predictive of substantial remission achieved during the subsequent 12 months. In the latter scenario, suPAR values might become useful as biomarker of FSGS disease activity as well.

This study of two distinct primary FSGS cohorts suggests that serial measurements of suPAR levels may provide a useful biomarker of response to treatment. Unlike the PodoNet cohort, in which the nature and timing of therapy was not coordinated with the blood sampling for suPAR measurements, FSGS CT offered the unique opportunity to assess the effect of different treatments because serum and plasma specimens were obtained prior to and after 26 weeks of treatment with MMF or cyclosporine A. The observations indicate that MMF therapy was associated with a significant decline in suPAR levels in contrast to the calcineurin inhibitor that increased serum suPAR concentration. This is supported by the cross sectional data from the PodoNet cohort in which patients treated with MMF exhibited significantly lower suPAR levels than patients treated with calcineurin inhibitor therapy. These findings suggest that while calcineurin inhibitors may have a beneficial effect in patients with FSGS, MMF could have a different biological effect on cells producing circulating factor(s). This raises the possibility that the two agents have distinct therapeutic targets and may act synergistically in the treatment of glomerular disease.

The relationship and clinical differences in pathogenesis and treatment responses between genetic and non-genetic cases of primary FSGS has long been a topic of discussion. It was reported, that recurrence after transplantation could also occur in genetic FSGS. In the study of FSGS patients with NPHS2 mutation, Caridi et al. found that the post-transplantation outcomes of these patients including the possibility of recurrence of proteinuria and responsive to plasmapheresis were similar to classical idiopathic FSGS. Their study suggested that a circulating permeability factor might exist in FSGS patients with NPHS2 mutation as well as in those without a genetic cause. Indeed, the same group further analyzed five patients with autosomal recessive SRNS(NPHS2) for serum glomerular permeability activity (Palb), and found high pre-transplant Palb in all cases, equivalent to values observed in idiopathic FSGS. They also found post-transplantation proteinuria was associated with high Palb, and both could be decreased by plasmapheresis. In the PodoNet cohort, circulating suPAR levels were significantly higher in familial FSGS and FSGS with documented NPHS2 mutations. This study suggests that suPAR may be a common FSGS factor that is superimposed on underlying genetic changes (e.g., FSGS associated mutations in NPHS1 and TRPC6).

In conclusion, following the initial identification of suPAR as a circulating permeability factor in primary FSGS, this study of two distinct FSGS cohorts confirms that a high circulating level of suPAR is characteristic of the majority of patients with primary FSGS. Though additional studies are warranted, this study suggests the potential additional role of suPAR as an independent biomarker of FSGS disease progression and/or response responsiveness.

Methods

FSGS Clinical Trial (FSGS-CT) Cohort

FSGS-CT is a randomized controlled study that compared the efficacy of cyclosporine (CSA) to the combination of mycophenolate mofetil (MMF) and dexamethasone. Key inclusion criteria were age 2-40 years, eGFR>40 ml/min per 1.73 m², biopsy-proven FSGS, and resistance to corticosteroid therapy. Exclusion criteria included secondary FSGS, obesity, or prior experimental therapy. All subjects received lisinopril or losartan in those who were intolerant of angiotensin converting enzyme inhibitor. Subjects were treated for 52 weeks. The primary outcome was normalization of proteinuria defined as a urine protein:creatinine ratio (Up/c)<0.2 in a first morning urine sample after 52 weeks of active treatment with the study medication(s). The main secondary outcome was based on the level of proteinuria at 78 weeks, six months after discontinuation of the study drugs. Subjects were seen 11 times during the treatment period and, at each visit, blood pressure was measured and blood and urine were obtained to determine serum creatinine, eGFR, albumin, cholesterol concentration, and proteinuria (Gipson et al., Kidney Int'l 80:868-878, 2011). The serum samples collected at baseline (W01) and 26 weeks (W26) on treatment (n=35 in each arm) were retrieved from the NIDDK Biorepository for suPAR measurement.

PodoNet Cohort

PodoNet is a consortium for clinical, genetic, and experimental study of steroid-resistant nephrotic syndrome (SRNS). The inclusion criteria are children (age 0-18 years old) with SRNS based on management protocols at the participating medical centers and adults with familial SRNS. Patients who were included into this study had biopsy proven FSGS (n=94). The treatment of subjects was clinically determined and managed by their attending physician.

Control Subjects

Plasma samples were available from 110 healthy Caucasian children and adolescents (female=55), who were 0-18 years old. These subjects were recruited from either primary school or high school in Rostock, and from the Medical Faculty of the University of Rostock, Germany. Children presenting at the University Children's Hospital Rostock for diagnostic workup either before minor surgery or secondary to non-inflammatory diseases like epilepsy and orthostatic complaints were also eligible. Children with growth disorders, a history of recent fracture or malnutrition, acute infections, elevated serum concentration of the C-reactive protein ($\geq 5$ mg/l) or creatinine ($\geq 2$ SD) at time of enrolment as well as those with metabolic disorders, chronic inflammatory diseases, and renal or hepatic disease were excluded. The study was approved by the Hospital Ethics Committee (HV-2009-003), and informed consent was obtained from parents and/or participants, if appropriate. Serum and EDTA-plasma were aliquoted, then stored at $-80°$ C. for later analysis. suPAR levels in healthy adult controls were included in the original study.

Serum suPAR Assay

The measurement of serum suPAR was performed using a Quantikine human uPAR immunoassay kit (R&D Systems).

Statistical Analysis

Demographic and clinical characteristics of patient and control subjects were compared using $\chi^2$ test for categorical variables and Student t tests for continuous variables. Multiple regression analysis for circulating suPAR with other variables was performed with SPSS. Data were expressed as mean±standard error of mean (SEM). All statistical tests were two tailed and P<0.05 was considered significant.

Example 3

Focal segmental glomerulosclerosis (FSGS) recurs after kidney transplantation in approximately one-third of affected individuals and can lead to allograft loss. The effect of suPAR on the ultrastructural changes in podocytes was investigated during recurrent or de novo FSGS. The impact of therapy on podocyte structure was determined.

A retrospective study was conducted at a single center of 25 adults who underwent renal transplantation and developed recurrent or de novo FSGS. Histopathologic changes were reviewed, and suPAR levels were correlated with ultrastructural podocyte changes. Their clinical course and the effect of therapy on podocyte effacement were evaluated.

Baseline allograft biopsies showed only five subjects with changes consistent with FSGS on light microscopy, and the degree of podocyte effacement ranged from 15% to 100%. Mean (±SD) pre-treatment suPAR levels were greater among those with severe foot process effacement ($\geq 75$%) versus those with mild foot process effacement (<25%) (11,773 pg/ml±5,595 pg/ml vs. 5,070 pg/ml±1,277 pg/ml respectively; P=0.02). A median of 21 (IQR: 10-23) plasmapheresis sessions was administered. Twelve patients received rituximab. Among responders, mean serum creatinine improved from 3.1 mg/dl±2.5 mg/dl to 1.9 mg/dl±0.6 mg/dl (P=0.048). Mean proteinuria declined from 5.3 g/g±5.9 g/g to 1.6 g/g±1.6 g/g (P=0.01) and mean foot process effacement decreased from 54%±35% to 23%±23% (P=0.007).

The initial pathologic manifestation of FSGS post-transplant is podocyte foot process effacement. The degree of the effacement is closely linked to the level of pre-treatment suPAR. Response to therapy improves foot process effacement.

Participant demographic and clinical characteristics are shown in Table 3. The median time to FSGS diagnosis was 48 days (interquartile range (IQR) from 4 days to 350 days) after kidney transplantation. Prior to treatment, twenty (80%) of the recipients had eGFRs below 60 ml/min per 1.73 m² while thirteen (52%) had 3 g/g or greater of proteinuria. The mean duration of follow-up was 16.0 months±20.1 months. Mean±standard deviation (SD).

TABLE 3

| Demographic and Clinical Characteristics (n = 25) | |
|---|---|
| Male, n (%) | 13 (52) |
| Black, n (%) | 13 (54) |
| Mean age at transplantation, years ± SD | 43 ± 12 |
| Mean age at FSGS diagnosis, years ± SD | 33 ± 11 |
| Median duration on dialysis, years (IQR) | 2 (0.5-3) |
| Pre-transplant urination, n (%) | 15 (60) |
| Primary pre-transplant diagnosis, n (%) | |
| FSGS | 21 (84) |
| Other | 3 (12) |
| Unknown | 1 (4) |
| No. of transplants at time of FSGS recurrence, n (%) | |
| 1 | 18 (72) |
| 2 | 4 (16) |
| 3 | 3 (12) |
| Living Donor, n (%) | 15 (60) |
| Related | 4 (16) |
| Unrelated | 11 (44) |
| ABO-incompatible transplant, n (%) | 5 (20) |
| Median time to treatment post-transplant, days (IQR) | 48 (4-350) |
| Median proteinuria, g/g (IQR) | |
| Pre-transplantation | 2.3 (1.1-7.7) |
| Pre-treatment | 3.9 (1.8-7.3) |
| Median pre-treatment serum creatinine, mg/dl (IQR) | 2.2 (1.8-4) |
| Median pre-treatment eGFR, ml/min|1.73 m² (IQR) | 35.1 (22.7-43.4) |
| Median pre-treatment suPAR, pg/ml (IQR) | 6714 (5821-8557) |

Twenty-four subjects had baseline (at time of post-transplant FSGS diagnosis) renal biopsies available; in seventeen subjects the biopsy was performed before plasmapheresis initiation and in six shortly after the initiation of the therapy (mean of 5 days after treatment initiation, range: 3-9 days) to assess the baseline degree of foot process effacement; one individual did not have renal biopsy and another one did not receive plasmapheresis therapy. On baseline renal biopsy, five of the subjects had histopathological changes consistent with FSGS on light microscopy (segmental sclerosis and hylain deposition), 19 did not have any FSGS changes on light microscopy in initial biopsy; the foot process effacement ranged from 15% to 100%. On Twenty-two individuals had at follow up after therapy; four of the subjects who had light microscopic changes continued to have the same changes, and one did not have any FSGS changes on light microscopy. But four additional subjects developed light microscopic changes on follow up biopsy after therapy, three of them did not respond to therapy and lost their allograft shortly after the recurrence, and one had only partial response to therapy and lost allograft a year later.

Pre-treatment suPAR levels significantly correlated with the severity of foot process effacement in a graded fashion (Table 4). The mean suPAR levels were more than two-fold higher among those with severe versus those with mild foot process effacement (11,773 pg/ml±5,595 pg/ml vs. 5,070 pg/ml±1,277 pg/ml respectively; P=0.02).

TABLE 4

Mean Pre-Treatment suPAR Level by Degree of Effacement on Baseline Kidney Biopsy (n = 14)

| Mean Podocyte Effacement | Mean suPAR, pg/ml (SD) |
|---|---|
| ≤25% (n = 5) | 5,070 (1,277) |
| from 26% to 74% (n = 4) | 8,109 (4,335) |
| ≥75% (n = 5) | 11,773 (5,595) |

*P-value for differences in means = 0.02

Treatment with plasmapheresis (PXP) started at the time of FSGS recurrence or de novo manifesting by the onset or worsening of proteinuria. Subjects completed a median of 21 plasmapheresis sessions (IQR: 10-23). Twelve subjects were refractory to plasmapheresis and received adjunctive rituximab infusion. Eight (32%) subjects had complete remission, and an additional 12 (48%) individuals achieved partial remission. With treatment (Table 5), the overall mean serum creatinine improved from 3.1 mg/dl±2.3 mg/dl to 2.1 mg/dl±1.2 mg/dl (P=0.07), and the mean eGFR improved from 35.6 ml/min±19.4 ml/min to 46.0 ml/min±24.3 ml/min per 1.73 m² (P=0.01). Additionally, among responders the serum creatinine declined further from 3.1 mg/dl±2.5 mg/dl to 1.9 mg/dl±0.6 mg/dl (P=0.48).

TABLE 5

Change in Renal Parameters Pre-Post Treatment Overall

|  | Mean Pre ± SD | Mean Post ± SD | P-value |
|---|---|---|---|
| Mean Foot Process Effacement, % | | | |
| First biopsy (n = 24) | 59 ± 33 | | |
| Overall (n = 22) | 60 ± 33 | 29 ± 30 | 0.002 |
| PXP alone (n = 12) | 70 ± 31 | 35 ± 30 | 0.01 |
| PXP + rituximab (n = 10) | 49 ± 32 | 21 ± 27 | 0.07 |
| Serum Creatinine, mg/dl | | | |
| Overall (n = 25) | 3.1 ± 2.3 | 2.1 ± 1.2 | 0.07 |
| PXP alone (n = 12) | 3.1 ± 1.9 | 2.1 ± 1.4 | 0.16 |
| PXP + rituximab (n = 12) | 3 ± 2.7 | 2.1 ± 0.88 | 0.28 |

TABLE 5-continued

Change in Renal Parameters Pre-Post Treatment Overall

|  | Mean Pre ± SD | Mean Post ± SD | P-value |
|---|---|---|---|
| Proteinuria, g/g | | | |
| Overall (n = 24) | 5.4 ± 5.4 | 4.4 ± 9.4 | 0.6 |
| PXP alone (n = 12) | 6.4 ± 6.9 | 2.1 ± 3.1 | 0.07 |
| PXP + rituximab (n = 12) | 4.4 ± 3.1 | 6.6 ± 12.5 | 0.57 |

|  | Peak | Most recent | |
|---|---|---|---|
| Proteinuria, g/g | | | |
| Overall (n = 24) | 10.9 ± 11.4 | 4.6 ± 10 | 0.05 |
| PXP alone (n = 12) | 9.3 ± 9.6 | 2.3 ± 5.4 | 0.045 |
| PXP + rituximab (n = 12) | 12.5 ± 12.7 | 7 ± 12.7 | 0.3 |

Among those who attained complete or partial remission (Table 6), mean proteinuria declined significantly after treatment from 5.3 g/g±5.9 g/g to 1.6 g/g±1.6 g/g (P=0.01). In contrast, individuals who did not respond to treatment had persistent proteinuria, ranging from 4.2 g/g to 17.0 g/g. Improvements in these clinical parameters correlated with observed changes in foot process effacement, which decreased from 54%±35% to 23%±23% (P=0.007) in subjects who achieved complete or partial remission, only one developed FSGS on light microscopy.

TABLE 6

Change in Renal Parameters Pre-Post Treatment in Responders

|  | Mean Pre ± SD | Mean Post ± SD | P-value |
|---|---|---|---|
| Mean Foot Process Effacement, % | | | |
| Overall (n = 17) | 54 ± 35 | 23 ± 23 | 0.007 |
| PXP alone (n = 10) | 67 ± 34 | 30 ± 26 | 0.017 |
| PXP + rituximab (n = 7) | 34 ± 27 | 14 ± 14 | 0.1 |
| Serum Creatinine, mg/dl | | | |
| Overall (n = 20) | 3.1 ± 2.5 | 1.9 ± 0.6 | 0.048 |
| PXP alone (n = 11) | 3.1 ± 2 | 1.7 ± 0.5 | 0.047 |
| PXP + rituximab (n = 12) | 3 ± 2.96 | 2.1 ± 0.7 | 0.38 |
| Proteinuria, g/g | | | |
| Overall (n = 20) | 5.3 ± 5.9 | 1.6 ± 1.6 | 0.01 |
| PXP alone (n = 11) | 6.3 ± 7.2 | 1.3 ± 1.7 | 0.04 |
| PXP + rituximab (n = 9) | 4.1 ± 3.4 | 1.9 ± 1.4 | 0.1 |

|  | Peak | Last | |
|---|---|---|---|
| Proteinuria, g/g | | | |
| Overall (n = 20) | 8.3 ± 8 | 1.2 ± 1 | 0.0005 |
| PXP alone (n = 11) | 8.8 ± 9.8 | 0.7 ± 0.7 | 0.017 |
| PXP + rituximab (n = 9) | 7.6 ± 4.9 | 1.7 ± 1.2 | 0.005 |

Discussion

This study demonstrates that the level of circulating suPAR prior to treatment of recurrent or de novo FSGS after renal transplantation significantly correlates with the severity of podocyte foot process effacement in the renal allograft at time of FSGS diagnosis. Secondly, our study established that the initial pathologic finding of recurrent and de novo FSGS in the renal allograft is podocyte foot process effacement, detected by electron microscopy, that can extend from mild (≤25%) to severe 75%) and in some cases complete effacement in the absence of light microscopic changes. Thirdly, we demonstrated that complete or partial response to plasmapheresis with or without rituximab resulted in a significant improvement in podocyte foot process effacement.

Our data extends the recently discovered role of suPAR in FSGS. In the study by Wei and colleagues, approximately two-thirds of subjects with primary FSGS had significantly elevated concentrations of suPAR compared to healthy subjects and those with other primary nephrotic syndromes. Moreover, the highest pre-transplant suPAR levels were noted among subjects with FSGS who went on to develop FSGS recurrence after renal transplantation. Our study builds upon these findings by demonstrating that among recipients with recurrent or de novo FSGS following renal transplantation, suPAR levels correlate with ultrastructural changes in podocyte structure in humans.

In addition, our findings demonstrate the potential importance of measuring suPAR levels to predict the FSGS recurrence risk and estimate the amount of possible damage in podocytes of the renal allograft. Based on experimental mouse models, suPAR's effects on foot processes are through binding and activation of β3 integrin expressed on podocytes. Taken in the context of variable response to plasmapheresis with or without rituximab, however, prospective studies are needed to determine whether the gene that encodes for β3 integrin (ITGB3) in the recipient or allograft kidney also has prognostic bearing on recurrent FSGS and response to treatment. It also remains to be established whether plasmapheresis and rituximab-induced improvement in foot process effacement is paralleled by a decrease in circulating suPAR levels and to establish which treatment strategy is superior in achieving a reduction in circulating suPAR levels.

Some have suggested that the most immediate finding in recurrent FSGS is foot process effacement; there is limited clinical data, however, to confirm this. While several case reports have shown foot process effacement in renal transplant recipients with recurrent FSGS, only one reported electron microscopy changes prior to institution of therapy on a single patient with immediate recurrence of FSGS after deceased donor kidney transplantation. In this report, the graft biopsy at one hour following transplantation showed minor glomerular abnormalities with partial foot process effacement on electric microscopy. Protocol biopsy at three months for persistent proteinuria showed obvious FSGS under light microscopy. Renal allograft biopsy after one year showed recovery of foot process effacement but increased global sclerosis. Although we recently reported that the degree of foot process effacement in post-reperfusion biopsies in FSGS patients at high-risk for recurrent disease may predict recurrent proteinuria after transplantation, these data will need to be validated in a different population that is inclusive of adult patients with FSGS.

Our study represents the largest case series to date confirms that the earliest detectable change in recurrent FSGS after renal transplantation is foot process effacement and demonstrates that early diagnosis and treatment of recurrent FSGS can result in improvement or resolution of foot process effacement and clinical renal parameters such as allograft renal function and proteinuria.

In summary, we demonstrate that pre-treatment suPAR levels were associated with the severity of podocyte foot process effacement at the time of FSGS diagnosis post-transplantation. Additionally, we establish that the podocyte foot process effacement detected by electron microscopy is the first ultrastructural change during human recurrent FSGS and de novo after kidney transplantation. Furthermore, a complete or even partial response to plasmapheresis with or without rituximab resulted in a complete or partial recovery of foot process effacement. These findings highlight the need for prospective trials to determine whether lowering of suPAR levels prior to or following renal transplantation prevents FSGS recurrence and the need for additional studies to determine whether other recipient and donor factors impact risk for FSGS recurrence. In addition, our study also supports the need to evaluate the role of electron microscopy changes to monitor response to and determine appropriate duration of therapy.

Methods

Study Design and Population

We conducted a retrospective observational study of all adult renal transplant recipients who underwent renal transplantation between Jan. 1, 2003 to Dec. 31, 2011, and developed recurrent or de novo FSGS after kidney transplantation at a single tertiary hospital. We identified 105 renal transplant recipients aged 18 years and older. Ninety-three had native kidney biopsy-proven FSGS; 12 having a probable FSGS diagnosis. Twenty-five individuals developed de novo FSGS (n=4) and recurrent FSGS (n=21) following renal transplantation. Recurrent FSGS was defined by the presence of proteinuria (more than 1 g/24 hours) in individuals who were anuric prior to renal transplantation (eight anuric and two unknown) or worsening proteinuria among those who were not anuric prior to renal transplantation (n=15). De novo FSGS was defined as the new onset of proteinuria following renal transplantation in a recipient whose primary cause of ESRD was not attributed to FSGS. The diagnosis was confirmed by the presence of podocyte foot process effacement on the allograft biopsy obtained prior to or within 14 days of treatment commencement. The Johns Hopkins University School of Medicine Institutional Review Board approved this study.

Data Collection

Socio-demographic and clinical data were abstracted from patient medical records using double data entry from the time of renal transplantation to three years following renal transplantation or the last available clinical follow-up. Donor clinical characteristics collected included donor vital status, relatedness to the recipient, and ABO-compatibility with recipient. Recipient clinical characteristics included age at FSGS diagnosis, primary cause of ESRD, number of prior renal transplantations, duration among those receiving dialysis, serum creatinine and proteinuria defined by urine protein-to-creatinine ratio. Glomerular filtration rate (eGFR) was estimated using the CKD-Epi equation which adjusts for age, gender, and race (Levey et al., Ann. Intern. Med. 150:604-612, 2009). Recipients were treated with plasmapheresis. Those with persistently significant proteinuria were also given one or two rituximab infusions. Complete response was defined by a decrease in proteinuria to below 1 g/g upon completion of the treatment course and/or on the last available quantification of proteinuria. Partial response to therapy was defined as a decline in proteinuria at the end of treatment by 50% from the peak proteinuria level, but with proteinuria remaining 1 g/g or greater at the end of treatment. Renal histopathology was assessed by a renal pathologist using light microscopy, immunofluorescence and electron microscopy. The degree of podocyte foot process effacement was based upon biopsy reports as well as secondary assessments of the electron microscopy by a second renal pathologist blinded to the original biopsy report and the recipient's outcome. These two assessments were then averaged to obtain the mean podocyte foot process effacement, which was categorized as <25% (mild), 25%-74% (moderate), and 75% or greater (severe). Baseline electron microscopy results were obtained from renal biopsies performed prior or shortly after the initiation of therapy. Post-treatment foot process effacement was assessed from renal biopsies performed following completion of the plasmapheresis sessions or after the rituximab infusion in refractory cases. Among recipients with stored serum available prior to treatment initiation, suPAR levels were measured using the Quantikine human uPAR immunoassay (R&D Systems) following the manufacturer's protocol at the University of Miami School of Medicine.

Statistical Analysis

Descriptive analyses were performed to evaluate distributions of the recipients' baseline sociodemographic and clinical characteristics. The pre-treatment mean suPAR levels were compared across the three categories of baseline foot process effacement using Kruskal-Wallis test. The change in mean podocyte effacement, kidney function, proteinuria, and suPAR levels from baseline to post-treatment were then evaluated using paired Student t-test. These comparisons were conducted using the overall study population and then restricted only to recipients who attained partial or complete response to treatment. All statistical analyses were performed using Stata/MP version 11.2 (StataCorp).

Patents, patent applications, and other publications cited herein are incorporated by reference in their entirety.

All modifications and substitutions that come within the meaning of the claims and the range of their legal equivalents are to be embraced within their scope. A claim using the transition "comprising" allows inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. An immunosorbent cartridge comprising:
   (i) an inlet;
   (ii) a support;
   (iii) one or more suPAR-specific antibodies or functional portions thereof;
   (iv) an outlet;
   (v) a housing that contains the support therein; and
   (vi) a fluid path through the housing that connects the inlet and the outlet;
   wherein the one or more antibodies or functional portions thereof are disposed within the housing; wherein the cartridge is configured for insertion into an apheresis apparatus; and wherein suPAR in a fluid phase, which is comprised of soluble blood components, enters at the inlet, follows the fluid path through the housing, and exits at the outlet, is immobilized through formation of an immune complex between the suPAR and the antibodies or functional portions thereof and their attachment to the support.

2. The cartridge of claim 1, wherein the cartridge is able to bind from 2 µg to 10 µg of suPAR.

3. The cartridge of claim 1, wherein the support is selected from the group consisting of at least one fluid-permeable membrane, one or more porous fiber(s), and a plurality of particles.

4. The cartridge of claim 1, wherein the housing is configured for at least membrane filtration or column chromatography.

5. The cartridge of claim 1, wherein the antibody or the functional portion thereof is reversibly attached to at least the support.

6. The cartridge of claim 1, wherein the antibody or the functional portion thereof is irreversibly attached to the support.

7. The cartridge of claim 1, which further comprises an aseptic packaging that surrounds the housing to maintain it, the inlet, and the outlet in sterile and pyrogen-free conditions.

8. The cartridge of claim 1, wherein the one or more suPAR-specific antibodies or functional portions thereof is unbound to the support within the housing until formation of an immune complex between the suPAR and the antibodies or functional portions thereof.

9. A method of removing soluble urokinase receptor (suPAR) from the circulation of a subject, the method comprising:
   (a) contacting, outside of the body of the subject, a fluid phase from the circulation of the subject and comprising suPAR and other plasma proteins, with one or more suPAR-specific antibodies or functional portions thereof under binding conditions, to thereby form an immune complex comprising suPAR bound to the suPAR-specific antibodies or functional portions thereof;
   (b) separating the immune complex from at least some of the other plasma proteins not complexed in the fluid phase outside the body of the subject; and
   (c) returning the at least some of the other plasma proteins to the circulation of the subject.

10. The method according to claim 9 further comprising, before (b), immobilizing the immune complex on at least a support.

11. The method according to claim 9 further comprising, after (a), separating plasma proteins from at least cells selected from the group consisting of erythrocytes, leukocytes, thrombocytes, and combinations thereof.

12. The method according to claim 9 further comprising, before (a), separating plasma proteins from at least cells selected from the group consisting of erythrocytes, leukocytes, thrombocytes, and combinations thereof.

13. The method according to claim 9 further comprising, before (b), separating plasma proteins from at least cells selected from the group consisting of erythrocytes, leukocytes, thrombocytes, and combinations thereof.

14. The method according to claim 9 further comprising adding one or more anti-coagulant(s) to the fluid phase.

15. The method according to claim 9, wherein the immune complex is separated from the at least some of the other plasma proteins by membrane filtration or column chromatography.

16. The method according to claim 9, wherein suPAR is removed from the circulation in from ten to 20 rounds of binding between a fluid phase and one or more suPAR-specific antibodies or functional portions thereof.

17. The method according to claim 9, wherein from at least 20% to at least 30% of the suPAR that is circulating in the patient prior to step (a) is removed in a single round.

18. The method according to claim 9, wherein the fluid phase is maintained under sterile and pyrogen-free conditions.

* * * * *

UNITED STATES PATENT AND TRADEMARK OFFICE
CERTIFICATE OF CORRECTION

PATENT NO.       : 9,867,923 B2                                           Page 1 of 1
APPLICATION NO.  : 14/116470
DATED            : January 16, 2018
INVENTOR(S)      : Jochen Reiser It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 581 days.

Signed and Sealed this
Twenty-fifth Day of September, 2018

Andrei Iancu
*Director of the United States Patent and Trademark Office*